United States Patent [19]

Atkinson et al.

[11] 4,153,715
[45] May 8, 1979

[54] INDOLYL AMINO ACIDS USEFUL AS ANTIHYPERTENSIVE AGENTS

[75] Inventors: Joseph G. Atkinson, Montreal; Clarence S. Rooney, Beaconsfield; Yves Girard, Dollard des Ormeaux, all of Canada; Edward L. Engelhardt, Gwynedd Valley, Pa.

[73] Assignee: Merck & Co., Inc., Rahway, N.J.

[21] Appl. No.: 825,013

[22] Filed: Aug. 16, 1977

Related U.S. Application Data

[62] Division of Ser. No. 657,827, Feb. 13, 1976, Pat. No. 4,065,572.

[51] Int. Cl.$^2$ ............... A61K 31/40; C07D 209/04; C07D 209/20
[52] U.S. Cl. .................. 424/274; 260/326.11; 260/326.14
[58] Field of Search ............... 424/274; 260/326.11, 260/326.14 R

[56] References Cited

U.S. PATENT DOCUMENTS 3,965,095  6/1976  Seemann ..................... 424/274
4,029,807  6/1977  Roldan et al. .................. 424/274

OTHER PUBLICATIONS

Chem. Abst. 58, 12664(d)-(1963)-Behringer, et al.
J. of Med. Chemistry 17(11), pp. 1223-1225 (1974), Zenker et al.
J. of Med. Chemistry 13, 741-742 (1970), Mikowski et al.

Primary Examiner—Albert T. Meyers
Assistant Examiner—D. W. Robinson
Attorney, Agent, or Firm—Donald J. Perrella; Daniel T. Szura

[57] ABSTRACT

A compound of the formula

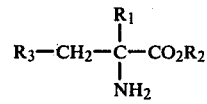

possesses antihypertensive activity. Also provided are methods for the preparation of the compounds as well as pharmaceutical formulations and methods for their use as antihypertensive agents.

5 Claims, No Drawings

INDOLYL AMINO ACIDS USEFUL AS ANTIHYPERTENSIVE AGENTS

This is a division of application Ser. No. 657,827, filed Feb. 13, 1976, now U.S. Pat. No. 4,065,572.

BACKGROUND OF THE INVENTION

This invention relates to antihypertensive agents and to methods for their preparation and use. More particularly, it relates to antihypertensive agents comprising substituted alanine compounds and to methods for the preparation and use of the antihypertensive agents.

DESCRIPTION OF THE PRIOR ART

The art records a long search for agents that are effective in treating hypertensive patients with acceptable clinical results and few, if any, side effects. There are, of course, a number of products available commercially which are useful for this purpose. One that has been extremely effective for the treatment of hypertension is the L form of 3-(3,4-dihydroxyphenyl)-2This The compound and its method of use are described in U.S. Pat. No. 3,344,023, issued in 1967. While a number of other compounds are well known in the art as antihypertensive drugs, the search continues for even more effective agents.

The compositions of the present invention are also alanine derivatives as are those described above, but are distinctly different in structure from prior art compounds.

OBJECT OF THE INVENTION

It is, accordinly, an object of the present invention to provide new compounds that are useful as antihypertensive agents.

A further object of the invention is to provide methods for the preparation of these new compounds.

Another object is to provide pharmaceutical compositions for administering these substituted alanine compounds.

A still further object of the invention is to provide methods for the treatment of subjects suffering from hypertension.

These and other objects and advantages of the present invention will become apparent from the following description.

SUMMARY OF THE INVENTION

In satisfaction of the foregoing objects and advantages, there are provided by this invention novel antihypertensive agents of the following general formula:

$$R_3-CH_2-\underset{\underset{NH_2}{|}}{\overset{\overset{R_1}{|}}{C}}-CO_2R_2$$

wherein $R_1$ and $R_2$ are hydrogen or lower alkyl and $R_3$ may be: (a) a substituted benzene ring of the following general formula:

wherein $Y_1$ and $Y_2$ are as specified in detail below; or (b) a substituted or unsubstituted benzoheterocyclic ring of the following general formula:

in which the specific benzoheterocyclic rings and the substituents are as specified in detail below; or (c) a substituted or unsubstituted heterocyclic ring of the following general formula:

in which the heterocyclic rings and the substituents thereon are as specified in detail below.

The foregoing general formulas are intended to include the racemic mixtures, the D and L enantiomorphs, and the pharmaceutically acceptable carboxylate salts and acid addition salts. Also provided are methods for the preparation of the compounds of the foregoing general formulas as well as pharmaceutical formulations, and methods for their use in the treatment of subjects suffering from hypertension to effect blood pressure lowering in these subjects.

DETAILED DESCRIPTION

As pointed out above, the invention is concerned with new antihypertensive agents which have been found to have significant antihypertensive activity and thus are very suitable for lowering the blood pressure of subjects suffering from hypertension. The antihypertensive agents may be best described as comprising a compound of the following general structural formula:

$$R_3-CH_2-\underset{\underset{NH_2}{|}}{\overset{\overset{R_1}{|}}{C}}-CO_2R_2$$

wherein $R_1$ and $R_2$ may be hydrogen or alkyl of from 1 to 3 carbon atoms, and $R_3$ may be: (a) a substituted benzene ring of the following general formula:

wherein $Y_1$ and $Y_2$ are the same or different and are selected from hydrogen, cyanoamino, carboxyl, cyano, thiocarbamoyl, aminomethyl, guanidino, hydroxy, methanesulfonomido, nitro amino, methanesulfonyloxy, carboxymethoxy, or methoxy or a substituted or unsubstituted 5-membered heterocyclic ri benzoheterocyclic or dibenzoheterocyclic ring containing one or more nitrogen or sulfur atoms. Specific examples of such heterocyclic rings are pyrrol-1-yl, 2-carboxypyrrol-1-yl, 2-amino-imidazol-1-yl, imidazol-2-ylamino, indol-1-yl, carbazol-9-yl, 4,5-dihydro-4-hydroxy-4-trifluoromethylthiazol-2-yl, 4-trifluoromethylthiazol-2-yl, imidazol-2-yl and 4,5-dihydroimidazol-2-yl; or (b) a substituted or unsubstituted benzoheterocyclic ring of the following general formula:

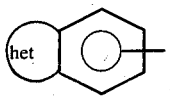

in which the benzoheterocyclic ring is selected from indolin-5-yl, 1H-2-oxindol-5-yl, indol-5-yl, 2-mercaptobenzimidazol-5(6)-yl, 2-aminobenzimidazol-5(6)-yl, 2-methanesulfononamidobenzimidazol-5(6)-yl, 1H-benzoaxazol-2-on-6-yl, 2-aminobenzothiazol-6-yl, 2,1,3-benzothiadiazol-5-yl, 1,3-dihydro-2,2-dioxo-2,1,3-benzothiadiazol-5-yl, 1,3-dihydro-1,3-dimethyl-2,2-dioxo-2,1,3-benzothiadiazol-5-yl, 4-methyl-2(1H)-oxoquinolin-6-yl, quinoxalin-6-yl, 2-hydroxyquinoxalin-6-yl, 2-hydroxyquinoxalin-7-yl, 2,3-dihydroxyquinoxalin-6-yl and 2,3-dihydro-3(4H)-oxo-1,4-benzoxazin-7-yl; or (c) a substituted or unsubstituted heterocyclic ring of the following general formula:

in which the heterocyclic ring is selected from 5-hydroxy-4H-pyran-4-on-2-yl, 2-hydroxypyrid-4-yl, 2-aminopyrid-4yl, or tetrazolo[1,5-a]pyrid-7-yl.

It is to be understood that the present invention is directed to not only the racemic mixtures, but also the D and L enantiomorphs. Also the invention is inclusive of the pharmacologically acceptable carboxylate salts such as those of Na, K, Ca and NH4 and the pharmacologically acceptable acid-addition salts formed with pharmaceutically acceptable acids.

Specific compounds of the present invention include the following:
4-cyanoamino-α-methylphenylalanine
3-carboxy-α-methylphenylalanine   -methylphenylalanine
4-(aminomethyl)-α-methylphenylalanine
4-guanidino-α-methylphenylalanine
3-hydroxy-4-methanesulfonamido-α-methylphenylalanine
4-amino-3-methanesulfonyloxy-α-methylphenylalanine
3-carboxymethoxy-4-nitro-α-methylphenylalanine
4-amino-α-methyl-3-nitrophenylalanine
3,4-diamino-α-methylphenylalanine
α-methyl-4-(pyrrol-1-yl)phenylalanine
4-(2-aminoimidazol-1-yl)-α-methylphenylalanine
4-(imidazol-2-ylamino)-α-methylphenylalanine
4-(4,5-dihydro-4-hydroxy-4-trifluoromethyl-thiazol-2-yl)-α-methylphenylalanine
α-methyl-4-(4-trifluoromethylthiazol-2-yl)phenylalanine
α-methyl-3-(4-trifluoromethylthiazol-2-yl)-phenylalanine
3-cyano-α-methylphenylalanine
α-methyl-3-(4-trifluoromethylthiazol-2-yl)tyrosine
4-(imidazol-2-yl)-α-methylphenylalanine
4-(4,5-dihydroimidazol-2-yl)-α-methylphenylalanine
3-imidazoly-2-yl)-α-methylphenylalanine
3-(4,5-dihydroimidazol-2-yl)-α-methylphenylalanine
4-(imidazol-2-yl)phenylalanine
4-(4,5-dihydroimidazol-2-yl)phenylalanine
3-(imidazol-2-yl)phenylalanine
3-(2,3-dihydro-1H-indol-5-yl)-α-methylalanine
α-methyl-3-(1H-2-oxindol-5-yl)alanine
3-(1H-indol-5-yl)-α-methylalanine
3-(benzimidazol-2-thione-5-yl)-αmethylalanine
3-(2-aminobenzimidazol-5-yl)-2-methylalanine
2-methyl-3-(benzoxazol-2-on-6-yl)alanine
3-(2-aminobenzothiazol-6-yl)-2-methylalanine
3-(2-aminobenzothiazol-6-yl)alanine
2-methyl-3-(2,1,3-benzothiadiazol-5-yl)-alanine
3-(1,3-dihydrobenzo-2,1,3-thiadiazol-5-yl)-2-methylalanine 2,2-dioxide
3-(1,3-dihydrobenzol-2,1,3-thiadiazol-5-yl)-alanine 2,2-dioxide
3-(1,3-dihydro-1,3-dimethylbenzo-2,1,3-thiadiazol-5-yl)-2-methylalanine 2,2-dioxide
α-methyl-3-[4-methyl-2(1H)-oxoquinolin-6-yl]alanine
3-[4-methyl-2(1H)-oxoquinolin-6-yl]alanine
2-methyl-3-(quinoxalin-6-yl)alanine
2-methyl-3-(2-hydroxyquinoxalin-6-yl)alanine
2-methyl-3-(2-hydroxyquinoxalin-7-yl)alanine
3-(2,3-dihydroxyquinoxalin-6yl)-2-methyalanine
3-(quinoxalin-6-yl)alanine
3-(2,3-dihydroxyquinoxalin-6-yl)alanine
3-(1,4-benzoxazin-3-one-7-yl)-2-methylalanine
3-(1,4-benzoxazin-3-one-7yl)alanine
3-(5-hydroxy-4H-pyran-4-on-2-yl)-2-methylalanine
3-(2-hydroxy-4-pyridyl)-2-methylalanine
3-cyano-α-methyltyrosine
4-(pyrrol-1-yl)phenylalanine
4-[2-(carboxy)pyrrol-1-yl]phenylalanine
α-methyl-3-(pyrrol1-yl)phenylalanine
3-hydroxy-α-methyl-4-(pyrrol-1-yl)phenylalanine
3-methoxy-α-methyl-4-(pyrrol-1-yl)phenylalanine
α-methyl-3-(pyrrol-1-yl)tyrosine
4-methoxy-α-methyl-3-(pyrrol-1-yl)phenylalanine
4-(indol-1yl)-α-methylphenylalanine
4-(carbazol-9-yl)-α-methylphenylalanine
3-(imidazol-2-yl)-α-methyltyrosine
2-methyl-3-(2-methanesulfonylamidobenzimidazol-5-yl)alanine
2-methyl-3-(2-amino-4-pyridyl)alanine
2-methyl-3[tetrazolo(1,5-a)-pyrid-7-yl]alanine The compounds of the present invention have been found to be effective in reducing elevated blood pressure in mammalian species, e.g., rats, and so are useful as antihypertensive agents. The compounds of the present invention are active either per se or in combination with α-hydrazino-α-loweralkyl-3,4-dihydroxyphenyl propionic acid or its salts or lower alkyl esters which compounds are themselves ineffective in reducing blood pressure in mammalian species. The compounds of the present invention may be administered either orally or parenterally and they can be compounded by the usual pharmaceutical methods for use in the lowering of blood pressure in subjects suffering from hypertension. Dosage units for the compounds may vary from about 0.05 to about 100 mg per kg per day. Normal dosage units for the compounds for oral administration will vary from about 10 to about 500 mg per kg per day. For oral administration to humans the dosage range is from about 0.1 to about 5 grams per day, preferably from about 0.5 to about 1.5 grams per day, usually in small but frequent dosages, e.g., in from 1 to 4 doses per day.

The antihypertensive agents of the present invention in the described dosages may be administered orally, however, other routes such as intraperitoneally, subcutaneously, intramuscularly or intravenously, may be employed.

For oral therapeutic administration, the active compounds of this invention may be incorporated with excipients and used in the form of tablets, troches, capules, elixirs, suspensions, syrups, wafers, chewing gums, and the like. The amount of active compound in such therapeutically useful compositions or preparations is such that a suitable dosage will be obtained.

For the compounds of the present invention not active per se, effective blood pressure lowering activity is obtained by administering them in the presence of from about 0.005 to about 200 mg per kg of α-hydrazino-α-loweralkyl-3,4-dihydroxyphenyl propionic acid or its salts or lower alkyl esters.

The tablets, troches, pills, capsules and the like may also contain the following: a binder such as gum tragacanth, acacia, corn starch or gelatin; and excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

As to the pharmaceutically acceptable salts, those coming within the purview of this invention include the pharmaceutically acceptable acid-addition salts. Acids useful for preparing these acid-addition salts include, inter alia, inorganic acids, such as hydrochloric, hydrobromic, sulfuric, and phosphoric acids, and organic acids such as maleic, fumaric, tartaric, citric, 2-acetoxybenzoic, salicyclic, succinic, or methanesulfonic acids. Also included within the invention are the pharmacologically acceptable carboxylate salts such as those of Na, K, Ca and NH$_4$.

The following examples illustrate the present invention without, however, limiting the same thereto. Unless indicated otherwise, all temperatures are expressed in degrees Celsius.

EXAMPLE 1

D,L-4-Cyanoamino-α-methylphenylalanine hydrate

To a solution of 3.2 g. (12 mmoles) of D,L-4-amino-α-methylphenylalanine dihydrochloride [Saari, et al., J. Med. Chem., 10, 1008 (1967)] and 5.05 g. (63 mmoles) of sodium acetate in 25 ml of water is added 1.6 g. (15 mmoles) of cyanogen bromide. After 30 minutes a fine white solid begins to separate, and 0.5 g. (5 mmoles) more of cyanogen bromide is added and the mixture left at room temperature for 16 hours. The product, which has crystallized, is obtained by filtration, washed with water and dried. Yield 2.02 g. (77%), m.p. 370°.

EXAMPLE 2

D,L3-carboxy-α-methylphenylalanine Hydrochloride

A. Methyl D,L-3-(3-cyanophenyl)-2-isocyano-2-methyl propionate

Methyl 2-isocyanopropionate (43.5 g, 385 mm) is added slowly to a suspension of sodium methoxide (20% excess) in 225 ml of dry dimethylformamide at −10 to −15°. The resultant solution is added slowly to a solution of 63 g 320 mmoles) of 3-cyanobenzyl bromide [J. von Braun and H. Reich, Ann. 445, 225 (1925)] in 200 ml of dry dimethylformamide at −10 to −15°. After the addition is complete the reaction mixture is allowed to reach room temperature. The mixture is added with stirring to a mixture of ice and water and the solid is filtered. The solid is suspended in 200 ml of water. The suspension is stirred for 1 hour, filtered, rinsed with water and dried in the air to yield methyl D,L-3-(3-cyano-phenyl)-2-isocyano-2-methyl propionate (56 g, 77%) m.p. 77°–80°.

B. DL-3-carboxy-α-methylphenylalanine Hydrochloride

The product from part A (4.0 g) and 35 ml of 12N hydrochloric acid is refluxed for 6 hours and the resulting white solid filtered, washed and dried to give the product as the hydrochloride salt (4.1 g, 90%) m.p. 280°–285°(dec.).

EXAMPLE 3

D,L-α-methyl-4-thiocarbamoylphenylalanine methyl ester

A. Methyl D,L-3-(4-cyanophenyl)-2-isocyano-2-methyl propionate

Methyl 2-isocyanopropionate (43.5 g, 385 mmoles) is added slowly to a suspension of sodium methoxide (20% excess) in 225 ml of dry dimethylformamide at −10 to −15°. The resultant solution is added slowly to a solution of 49.0 g (0.25 mole) of 4-cyanobenzyl bromide [Case, J. Am. Chem. Soc., 47, 1143 (1925)] in 200 ml of dry dimethyl formamide at −10 to −15°. After the addition is complete the reaction mixture is allowed to reach room temperature. The mixture is added with stirring to a mixture of ice and water and the solid is filtered. The solid is suspended in 200 ml of water, stirred for 1 hour, filtered, rinsed with water and dried in the air to yield methyl D,L-3-(4-cyanophenyl)-2-isocyano-2-methyl propionate (45.5 g, 80%) m.p. 90°–91°.

B. D,L-4-cyano-N-formyl-α-methylphenylalanine methyl ester

Methyl D,L-3-(4-cyanophenyl)-2-isocyano-2-methyl propionate (50 g 0.22 mole), prepared as described in step A is dissolved in 500 ml of ethyl acetate. To the resultant solution four milliliters of concentrated hydrochloric acid is added and the mixture is stirred at room temperature for 10–15 minutes. The ethyl acetate solution is rinsed with water until neutrality, dried, filtered and evaporated to dryness. The oily residue is tritutated with ether and allowed to crystallize. The solid is filtered, rinsed with cold ether and dried in the air to yield D,L-4-cyano-N-formyl-α-methyl phenylalanine methyl ester, 32.7 g (60%), m.p. 152°–153°.

C. D,L-4-N-formyl-α-methyl-4-thiocarbamoylphenylalanine methyl ester

D,L-4-cyano-N-formyl-α-methylphenylalanine methyl ester (5.0 g, 20.3 mmoles is dissolved in 150 ml of pyridine. To the resultant solution triethylamine (2.1 g) is added and hydrogen sulfide is bubbled through the solution for 2 hours. The mixture is stirred for 18 hours at room temperature, evaporated to dryness and the residue is dissolved in chloroform. The chloroform solution is rinsed with water, dried, filtered and evaporated to dryness to yield a gum. A layer of ether is added on top of the gum and the mixture is allowed to crystallize at room temperature for 48 hours. The solid is filtered, rinsed with ether and dried in the air to give D,L-N-formyl-α-methyl-4-thiocarbamoylphenylalanine methyl ester. 5.36 g (94%), m.p. 135°–137°.

D,L-α-methyl-4-thiocarbamoylphenylalanine methyl ester

To a solution (4.4 g, 15.7 mmoles) of D,L-N-formyl-α-methyl-4-thiocarbamoylphenylalanine methyl ester in 120 ml of methanol is added 5 ml of concentrated hydrochloric acid and the mixture is left to stand at room temperature for 3 days. The solution is evaporated to dryness, the residue dissolved in 100 ml of water which is washed with 2 × 50 ml of ethyl acetate. The aqueous phase is made basic with sodium bicarbonate, and extracted with 2 × 100 ml of ethyl acetate. The ethyl acetate extracts are dried, evaporated and the residue triturated with 15 ml of ether and the resulting solid filtered to yield 3.6 g (76%) of D,L-α-methyl-4-thiocarbamoylphenylalanine methyl ester, m.p. 126°–128°.

EXAMPLE 4

D,L-4-(aminomethyl)-α-methylphenylalanine dihydrochloride hydrate

A mixture of 6.0 g (24.4 mmoles) of D,L-4-cyano-N-formyl-α-methylphenylalanine methyl ester (prepared as described in step B of Example 3), 1.0 gm of Raney nickel and 150 ml of acetic anhydride is hydrogenated under 18.1 kg of hydrogen for a period of 6 hours. The reaction mixture is filtered from the catalyst and the filtrate evaporated to leave a thick oil which is heated to reflux in 150 ml of concentrated hydrochloric acid for 6 hours. The solution is evaporated to dryness and from the residue 3 × 50 ml of water and 4 × 50 ml of benzene are evaporated successively. The solid residue is finally filtered with aid of benzene and dried to give 6.15 g (90%) of D,L-4-(aminomethyl)-α-methylphenylalanine dihydrochloride hydrate, m.p. 178°–186° (dec.).

EXAMPLE 5

D,L-4-Guanidino-α-methylphenylalanine Dihydrochloride

A. D,L-N-acetyl-α-methyl-4-aminophenylalanine methyl ester

D,L-N-acetyl-α-methyl-4-nitrophenylalanine methyl ester, [Zenker et al., J. Med. Chem., 17, 1223 (1974)], (40 g, 143 mm) in methanol is hydrogenated at 3.1 kg/cm² over 5% palladium on charcoal. The solution is filtered and concentrated to yield 15.8 g of D,L-N-acetyl-α-methyl-4-aminophenylalanine methyl ester, m.p. 145°–148°. The mother liquors are evaporated to yield a further 17.8 g. of N-acetyl-α-methyl-4-aminophenyl alanine methyl ester. Total yield 94%.

B.
D,L-N-Acetyl-4-(3-benzoylquanidino)-α-methyl-phenylalanine methyl ester

D,L-N-Acetyl-α-methyl-4-aminophenylalanine methyl ester (3.0 g, 12 mmoles) is dissolved in 50 ml of methanol, dry hydrogen chloride is passed into the solution, and the solvent is removed in vacuo. The evaporation is repeated several times with methanol. The residue is dissolved in 25 ml of methanol and then refluxed for 24 hours with 1.76 g (12 mmoles) of benzoyl cyanamide. A further 352 mg (2 mmole) of benzoyl cyanamide is added and the solution refluxed a further 24 hours. The solution is evaporated in vacuo and the solids triturated with ethyl acetate to give 4.75 g of solids. The solids are further triturated with 50 ml of hot ethyl acetate to give 4.12 g (79.2%) of D,L-N-actyl-4-(3-benzoylguanidino)-α-methyl-phenylalanine methyl ester, m.p. 234°–245° (dec).

C. D,L-4-guanidino-α-methylphenylalanine dihydrochloride

D,L-N-acetyl-4-(3-benzoylguanidino)-α-methyl-phenylalanine methyl ester (3.45 g, 8 mmole) is refluxed for 6 hours in 160 ml. of 7N hydrochloric acid. The solution is extracted with 3 × 20 ml of diethyl ether to remove benzoic acid and the aqueous portion is evaporated. The residue is treated with 1:1 ethanol:benzene to afford a dry product, and finally triturated with hot ethanol to give 1.53 g (61.9%) of D,L-4-guanidino-α-methylphenylalanine dihydrochloride, m.p. 299°–303° (dec).

EXAMPLE 6

D,L-3-Hydroxy-4-methanesulfonamido-α-methyl-phenylalanine

A.
D,L-N-Formyl-3-hydroxy-4-nitro-α-methylphenylalanine methyl ester

In a 3 liter, 3-neck flask, equipped with a mechanical stirrer, drying tube and thermometer, 3-hydroxy-4-nitro benzyl chloride (140.5 g, 0.75 mole), prepared as described by S. B. Hanna et al., J. Chem. Soc. 221, (1961) is dissolved in dimethyl formamide (750 ml). The solution is cooled in an ice-bath and powdered sodium methoxide (40.5 g, 0.75 mole) is added over a 5-minute period. This flask is then cooled and maintained at −55°. In a separate flask, to a suspension of sodium methoxide (81 g, 1.5 moles) in dimethyl formamide (1.0 liter) kept at −55°, is added methyl 2-isocyanopropionate (171 g, 1.5 moles). The temperature is not allowed to rise above −50°. This solution is then added to the flask containing the anion of 3-hydroxy-4-nitrobenzyl chloride, always keeping the temperature at −50°. Over a period of 30 minutes, the temperature is allowed to reach −35° after which TLC analysis indicates complete disappearance of 3-hydroxy-4-nitrobenzyl chloride. Water (1000 ml) is then added and the mixture is extracted three times with ether to remove excess methyl 2-isocyanopropionate. The aqueous phase is acidified by addition of acetic acid (180 ml in 180 ml of water) and is extracted three times with ether. The organic phase is washed with water, dried over magnesium sulfate and concentrated under vacuum. The residual oil, dissolved in ethyl acetate (1.5 liters) and maintained at 0°, is hydrolyzed by adding concentrated hydrochloric acid (15ml) and stirring for a period of 10 minutes. The solution is washed with water, dried over magnesium sulfate and concentrated under vacuum to yield 155 g (73%) of a solid after trituration in petroleum ether, m.p. 113°–115°.

B.
D,L-3-Hydroxy-4-methanesulfonamido-α-methylphenylalanine

D,L-N-Formyl-3-hydroxy-4-nitro-α-methylphenylalanine methyl ester (14.1 g, 50 mmoles) dissolved in 50 ml methanol is hydrogenated over 5% palladium on charcoal on a Parr hydrogenator. After the absorption of hydrogen is over, the catalyst is filtered off and the solvent is evaporated under vacuum, leaving a thick red oil that is dissolved in acetone (200 ml) and water (20 ml). Methanesulfonyl chloride (22.2 g, 195 mmole) and potassium carbonate (27 g, 195 mmoles) are added and the reaction mixture is stirred for a period of 1 hour. The insolubles are filtered and washed with acetone. The filtrate is concentrated to yield a dark oily residue which is taken up in ethyl acetate, washed with dilute hydrochloric acid and with water. The organic layer is dried over magnesium sulfate and concentrated. The residue (6 g) is absorbed on a silica gel column and eluted with ethyl acetate yielding 5.5 g of a residue consisting of D,L-N-formyl-4-bis(methanesulfonyl)amino-3-methanesulfonyloxy-α-methylphenylalanine methyl ester. It is taken up in 50 ml of 5% sodium hydroxide and heated on a steam bath for 2 hours. The pH of the solution is adjusted to neutrality and the solution is passed through a Dowex 50W-X8 100–200 mesh H+ charged column. Elution with 5% ammonium hydroxide yields 1.64 g (11.4%) of D,L-3-hydroxy-4-methanesulfonamido-α-methylphenylalanine, m.p. 298° (dec.).

EXAMPLE 7
D,L-4-Amino-3-methanesulfonyloxy-α-methylphenylalanine dihydrochloride

A.
D,L-N-Formyl-3-methanesulfonyloxy-4-nitro-α-methylphenylalanine methyl ester To D,L-N-formyl-3-hydroxy-4-nitro-α-methylphenylalanine methyl ester prepared as in step A of Example 6 (5.64 g, 20 mmoles) in 100 ml acetone and 10 ml water is added methanesulfonyl chloride (5.56 g, 40 mmoles) and potassium carbonate (5.52 g, 40 mmoles). The mixture is stirred at room temperature for 15 minutes. The insolubles are filtered off and washed well with acetone. The filtrate is evaporated to a small volume, ether is added and the solution is washed three times with water. After the third washing, a solid crystallizes out and is filtered to yield 5.8 g (80%) of D,L-N-formyl-3-methanesulfonyloxy-4-nitro-α-methylphenylalanine methyl ester, m.p. 132°–134°.

B.
D,L-4-amino-3-methanesulfonyloxy-α-methylphenylalanine dihydrochloride D,L-N-Formyl-3-methanesulfonyloxy-4-nitro-α-methyl phenylalanine methyl ester (4.5 g, 12.5 mmoles) from step A, in 50 ml concentrated hydrochloric acid is heated on a steam bath for 3.5 hours. The reaction mixture is evaporated to dryness to leave 4.6 g of a residue that is dissolved in 30 ml concentrated hydrochloric acid. Stannous chloride dihydrate (19.5 g, 87 mmoles) in 30 ml concentrated hydrochloric acid is added to this solution. The mixture is heated on the steam bath for 1 hour and is then poured into 500 ml water. Hydrogen sulfide is bubbled through the solution to remove all tin ions. The insoluble tin sulfides are filtered and the filtrate is evaporated to dryness. Refluxing the residue in toluene to remove traces of water gives 3.6 g (80%) D,L-3-methanesulfonyloxy-4-amino-α-methylphenylalanine dihydrochloride, m.p. 162° (dec.).

EXAMPLE 8
D,L-3-Carboxymethoxy-4-nitro-α-methylphenylalanine Hydrochloride To D,L-N-formyl-3-hydroxy-4-nitro-α-methylphenylalanine methyl ester (prepared as in step A of Example 6) (2.8 g, 10 mmoles) in 10 ml dimethyl formamide is added potassium t-butoxide (1.5 g, 13.2 mmoles) while the temperature is maintained at 10° with an ice bath. Ethyl bromoacetate (1.8 g, 10.8 mmoles) in 10 ml dimethylformamide is then added dropwise and the resulting mixture is stirred for 3 hours at room temperature, and then poured onto 700 ml ether and washed several times with water. After drying over magnesium sulfate and concentration under vacuum, an oily residue (4.2 g) is obtained. A rapid purification by absorbing on silica gel and eluting with chloroform yields 3.8 g (92%) of D,L-N-formyl-3-carboethoxymethoxy-4-nitro-α-methylphenylalanine methyl ester. This intermediate (2.8 g, 7.8 mmoles) in 25 ml concentrated hydrochloric acid is heated on a steam bath for 2 hours. The volatiles are removed under vacuum and the residue is treated with toluene yielding 2.2 g (88%) of D,L-3-carboxymethoxy-4-nitro-α-methylphenylalanine hydrochloride, m.p. 250° (dec.).

EXAMPLE 9
D,L-4-Amino-α-methyl-3-nitrophenylalanine Dihydrochloride

A.
D,L-N-Acetyl-α-methyl-4-amino-3-nitrophenylalanine methyl ester

D,L-N-Acetyl-α-methyl-4-acetylamino-3-nitrophenylalanine methyl ester [Zenker et al., J. Med. Chem., 17, 1223, (1974)] (45.9 g, 0.136 moles) and sodium carbonate (17.3 g, 0.163 moles) in 75% methanol-water (1500 ml) are stirred at room temperature for 18 hours. The resulting precipitate is filtered and slurried with water to yield 34.4 g (86%) of D,L-N-acetyl-α-methyl-4-amino-3-nitrophenylalanine methyl ester, m.p. 189°–192°.

D,L-4-Amino-α-methyl-3-nitrophenylalanine Dihydrochloride

A mixture of 10.0 g (34 mmoles) of the product from step A and 150 ml of 12N hydrochloric acid is heated in a sealed glass reaction vessel at 135° for 1 hour. The reaction mixture is then evaporated to dryness and the residue further dried by repeated evaporation of benzene. The resulting residue is slurried with ether and filtered to give 10.36 g (98%) of D,L-4-amino-α-methyl-3-nitrophenylalanine dihydrochloride m.p. 239°–241° (dec.).

EXAMPLE 10
D,L-3,4-Diamino-α-methylphenylalanine Dihydrochloride

A mixture of 4.7 g (15 mmoles) of D,L-4-amino-α-methyl-3-nitrophenylalanine dihydrochloride (prepared as in step B of Example 9), 500 mg. of 10% palladium on charcoal and 250 ml of methanol is hydrogenated under 18 kg pressure for 1 hour. The reaction mixture is filtered, evaporated to dryness and the residue refluxed in toluene for 16 hours. Filtration and drying gives 3.3 g of D,L-3,4-diamino-α-methylphenylalanine dihydrochloride, m.p. 135°–140° (dec.).

EXAMPLE 11

D,L-α-Methyl-4-(pyrrol-1-yl)phenylalanine

A. D,L-N-formyl-α-methylphenylalanine methyl ester

Treating 35 g (153 mmoles) of D,L-α-methylphenylalanine methyl ester hydrochloride according to the method of Stein et al., J. Am. Chem. Soc., 77, 700 (1955), except substituting a formic-acetic anhydride mixture for acetic anhydride, there is obtained 27 g (80%) of D,L-N-formyl-α-methyl-phenylalanine methyl ester, m.p. 64°.

B. D,L-N-Formyl-α-methyl-4-nitrophenylalanine methyl ester

The product from step A, 10 g (45.3 mmoles), is added slowly to 25 ml of stirring $HNC_3$ (red, fuming) at −15°. After stirring for an additional hour at −15°, the mixture is added slowly to a vigorously stirred, ice-cold, saturated $NaHCO_3$ solution. The resulting precipitate is filtered, washed with $H_2O$, and washed with 25 ml of ether yielding 4.24 g, m.p. 108°. The mother liquors yield another 7.0 g (oil) of crude product. The total yield is 94%.

C. D,L-N-formyl-α-methyl-4-amino-phenylalanine methyl ester

D,L-N-formyl-α-methyl-4-nitrophenylalanine methyl ester 184 g (690 mmoles) in methanol is hydrogenated at 3.1 kg/cm² over 5% palladium on charcoal. The solution is filtered and evaporated to yield a gum. The gum is dissolved in 2N hydrochloric acid and extracted with ethyl acetate.

The acidic aqueous solution is rendered alkaline with sodium bicarbonate and extracted with ethyl acetate. The ethyl acetate solution is evaporated and the residue is crystallized from methanol to yield 79.5 g (48.5%) of D,L-N-formyl-α-methyl-4-aminophenylalanine methyl ester, m.p. 105°–108°.

D. D,L-N-formyl-α-methyl-4-(pyrrol-1-yl)phenylalanine methyl ester

A solution of 13.5 g (57 mmoles) of D,L-N-formyl-α-methyl-4-aminophenylalanine methyl ester (prepared as in step C) and 8.44 g (64 mmoles) of 2,5-dimethoxytetrahydrofuran in 60 ml of acetic acid is heated on the steam bath under nitrogen for thirty minutes. The mixture is cooled, 150 ml of water added and the aqueous mixture extracted with 6 × 150 ml of chloroform. The combined chloroform extracts are washed with water, dried over magnesium sulfate, filtered, and the fitrate evaporated to dryness in vacuo to give 19.4 of crude product. The crude residue is eluted from a silica gel column with chloroform and the residue after the removal of chloroform is triturated with low boiling petroleum ether to give 8.32 g (50%) of D,L-N-formyl-α-methyl-4-(pyrrol-1-yl)phenylalanine methyl ester, m.p. 118°–119°.

E. D,L-α-methyl-4-(pyrrol-1-yl)phenylalanine

D,L-N-formyl-α-methyl-4-(pyrrol-1-yl)phenylalanine methyl ester (7.9 g, 27.6 mmoles) is heated overnight under nitrogen on a steam bath in 75 ml of methanol and 16 ml of 7N sodium hydroxide solution. A further 4 ml of 7N sodium hydroxide solution is added and the solution is heated four hours longer on the steam bath. The mixture is evaporated in vacuo, the solid residue dissolved in 100 ml of water, and 6.78 g (113 mmoles) of acetic acid is added. The mixture is refrigerated and the solids collected. The solids are refluxed for 1 hour with water, filtered, the solids washed with ethanol, then diethyl ether, and dried for several hours in a vacuum oven at 60° to give 6.45 g (79.5%) of D,L-α-methyl-4-(pyrrol-1-yl)phenylalanine, m.p. 290°–293° (dec).

EXAMPLE 12

D,L-4-(2-Aminoimidazol-1-yl)-α-methylphenylalanine hydrochloride and
D,L-4-(imidazol-2-ylamino)-α-methylphenylalanine hydrochloride

A. D,L-N-Acetyl-4-cyanamido-α-methylphenylalanine methyl ester

D,L-N-Acetyl-4-amino-α-methylphenylalanine methyl ester (16 g, 64 mmoles) (prepared as in step A of Example 5) is suspended in 225 ml of water, then 4.8 ml of concentrated hydrochloric acid in 25 ml of water added, followed by 12.7 g (155 mmoles) of sodium acetate, and finally by 13.6 g (128 mmole) of cyanogen bromide. The mixture is left at room temperature for 0.5 hour during which time much solids are precipitated. The solids are collected and air dried to give 16.8 g (95.2%) of D,L-N-acetyl-4-cyanamido-α-methyl-phenylalanine methyl ester, m.p. 171.5°–173.5°.

B. D,L-N-Acetyl-α-methyl-4-thioureidophenylalanine methyl ester

D,L-N-Acetyl-4-cyanamido-α-methylphenylalanine methyl ester (16.8 g, 61 mmole) is dissolved in a solution of 350 ml of dry pyridine and 6.8 g (67.1 mmoles) of triethylamine. Dry hydrogen sulfide is passed in during 2 hours accompanied by stirring. The solvent is removed in vacuo, the residue triturated with chloroform, filtered, and dried to give 18.4 g (97.5%) of D,L-N-acetyl-α-methyl-4-thioureidophenylalanine methyl ester, m.p. 202°–204°.

C. D,L-N-Acetyl-α-methyl-4-(2-methyl-1-isothioureido)-phenylalanine methyl ester D,L-N-Acetyl-α-methyl-4-thioureidophenylalanine methyl ester (18.3 q, 59 mmole) is suspended in 350 ml of acetonitrile and treated with 7.4 g (64.9 mmole) of methyl fluorosulfonate. The mixture is stirred for 1 hour to effect solution. The solution is concentrated in vacuo and the residue partitioned between ethyl acetate and dilute sodium bicarbonate. The ethyl acetate extracts are dried over magnesium sulfate, evaporated to dryness, and the residue crystallized from ethyl acetate-diethyl ether to give 15.4 g (80.7%) of D,L-N-acetyl-α-methyl-4-(2-methyl-1-isothioureido) phenylalanine methyl ester, m.p. 156°–158.0° (dec.).

D. D,L-4-(2-Aminoimidazol-1-yl)-α-methylphenylalanine hydrochloride and
D,L-4-(imidazol-2-ylamino)-α-methylphenylalanine hydrochloride D,L-N-Acetyl-α-methyl-4-(2-methyl-1-isothioureido)phenylalanine methyl ester (15 g, 47.6 mmoles)

is heated for 14 hours at 83° with 63.3 g (476 mmoles) of 2-aminoacetaldehyde diethyl acetal. Excess of the acetal is removed by distillation in vacuo to give 20 g (ca theory) of D,L-N-acetyl-4-[2-(2,2-diethoxyethyl)-guanidino]phenylalanine methyl ester as an oil. This product is used without further purification in the next reaction.

D,L-N-Acetyl-4-[2-(2,2-diethoxyethyl)guanidino]-phenylalanine methyl ester (ca 20 g) is dissolved in 200 ml of 6N hydrochloric acid at room temperature and the solution is immediately evaporated to dryness in vacuo at a bath temperature maintained at 45°. The residue is dissolved in water, treated with ammonium hydroxide to a pH of 10, then extracted with chloroform, and the combined chloroform extracts dried over magnesium sulfate. The filtrate is evaporated and the residue crystallized from acetonitrile to afford 2.75 g of D,L-N-acetyl-4-(2-aminoimidazol-1-yl)-α-methyl-phenylalanine methyl ester (containing a small amount of its isomer), m.p. 179°–183°. This ester (2.75 g) is refluxed for 5 hours in 55 ml of concentrated hydrochloric acid to give 2.33 g of D,L-4-(2-aminoimidazol-1-yl)-α-methylphenylalanine hydrochloride [containing ca 10% of D,L-4-(imidazol-2-ylamino)-α-methylphenylalanine hydrochloride].

The residues obtained after removal of the crystalline D,L-N-acetyl-4-(2-aminoimidazol-1-yl)-α-methyl-phenylalanine methyl ester are refluxed for 6 hours in 125 ml of concentrated hydrochloric acid, then the solvent removed in vacuo, and the product triturated with ethanol. The ethanol extracts when treated with benzene, afford 424 mg of D,L-4-(imidazol-2-ylamino)-α-methylphenylalanine hydrochloride, m.p. above 360° (darkening over a wide range). The residues on further purification afford 6.2 g of a mixture of the hydrochlorides of D,L-4-(2-aminoimidazol-1-yl)-α-methylphenylalanine and D,L-4-(imidazol-2-ylamino)-α-methylphenylalanine.

The ammoniacial liquors from the initial acid hydrolysis are evaporated, the resulting residue dissolved in 125 ml of concentrated hydrochloric acid, and refluxed for 6 hours. The solution is evaporated, the crude product dissolved in ammonia, evaporated, the residue dissolved in water, and passed through a column of Dowex 50W-X4 50 –100 mesh cation exchange resin. The liquid is evaporated to dryness, the solids dissolved in dilute hydrochloric acid, treated with charcoal, filtered, and partially evaporated to give 1.19 g of pure D,L-4-(2-aminoimidazol-1-yl)-α-methylphenylalanine hydrochloride, m.p. 320° (dec). The mother liquors from these solids afford 2.25 g of 1:1 mixture of the hydrochlorides of D,L-4-(2-aminoimidazol-1-yl)-α-methylphenylalanine and D,L-4-(imidazol-2-ylamino)-α-methylphenylalanine.

EXAMPLE 13

D,L-4(4,5-dihydro-4-hydroxy-4-trifluoromethylthiazol-2-yl)-α-methylphenylalanine methyl ester

A.

D,L-4,5-dihydro-4-hydroxy-4-trifluoromethylthiazol-2-yl)-N-formyl-α-methylphenylalanine methyl ester To a suspension of 5.0 g (17.8 mmoles) of D,L-N-formyl-α-methyl-4-thiocarbamoylphenylalnine methyl ester (prepared as in step C of Example 3) in 60 ml of chloroform is added 5 g (26.2 mmoles) of 3-bromo-1,1,1-tricfluoroacetone. The starting material gradually goes into solution and an oil later separates with a slight evolution of heat. The mixture is stirred at 25° for 6 hours, evaporated to dryness and the residue is partitioned between 50 ml of water and 100 ml of ethyl acetate. A second extract of 100 ml of ethyl acetate is combined with the first and the whole is dried and evaporated. The residue is triturated with 20 ml of ether and the resulting solid filtered to yield 4.7 g (68%) of D,L-4-(4,5-dihydro-4-hydroxy-4-trifluoromethyl-thiazol-2-yl)-N-formyl-α-methylphenylalanine methyl ester, m.p. 160°–165°.

B.

D,L-4-(4,5-dihydro-4-hydroxy-4-trifluoromethythiazol-2-yl)-α-methylphenylalanine methyl ester To a solution of 4.7 g (12 mmoles) of D,L-4-(4,5-dihydro-4-hydroxy-4-trifluoromethylthiazol-2-yl)-N-formyl-α-methylphenylalanine methyl ester in 100 ml of methanol is added 5 ml of concentrated hydrochloric acid and the mixture stirred at 25° for 2 days and evaporated to dryness keeping the temperature below 25°. The residue is dissolved in 100 ml of water and the solution extracted with 100 ml of ethylacetate. The aqueous fraction is then made basic with solid sodium bicarbonate and extracted with 2 × 100 ml of ethyl acetate. The organic solution is dried and evaporated to leave an oil which on trituration with 20 ml of low boiling petroleum ether crystallizes. The crystals are recovered by filtration to yield 2.68 g (62%) of D,L-4-(4,5-dihydro-4-hydroxy-4-trifluoromethylthiazol-2-yl)α-methylphenylalanine methyl ester, m.p. 118°–120°.

EXAMPLE 14

D,L-α-Methyl-4-(4-trifluoromethylthiazol-2-yl)phenylalanine hydrochloride

A mixture of 4 g (10.2 mmoles) of D,L-4,5-dihydro-4-hydroxy-4-trifluoromethylthiazoly-2-yl)-N-formyl-α-methylphenylalanine methyl ester (prepared as in step A of Example 13) and 50 ml of concentrated hydrochloric acid is heated to reflux for 1 hour. The mixture is evaporated to dryness, 50 ml of benzene added and evaporated and the residue filterred with the aid of 50 ml of benzene. After drying, there is obtained 3.6 g (96%) of D,L-α-methyl-4-(4-trifluoromethylthiazol-2-yl)phenylalanine hydrochloride, m.p. 220°–230°.

EXAMPLE 15

D,L-α-methyl-3-(4-trifluoromethylthiazol-2-yl)phenylalanine hydrochloride

A. D,L-3-cyano-N-formyl-α-methylphenylalanine methyl ester

Methyl D,L-3-(3-cyanophenyl)-2-isocyano-2-methyl propionate (1 g, 4.4 mmoles) prepared according to step A of Example 2 is dissolved in 25 ml of ethyl acetate. To the resultant solution one milliliter of concentrated hydrochloric acid is added and the mixture is stirred at room temperature for 10–15 minutes. The ethyl acetate solution is rinsed with water until neutrality, dried, filtered and evaporated to dryness. The oily residue is triturated with ether and allowed to crystallize. The solid is filtered, rinsed with cold ether and dried in the air to yield D,L-3-cyano-N-formyl-α-methylphenylalanine methyl ester, 830 mg. (77%), m.p. 132°–134°.

B.

D,L-N-formyl-α-methyl-3-thiocarbamoylphenylalanine methyl ester

D,L-3-cyano-N-formyl-α-methylphenylalanine methyl ester (25 g, 98.5 mmoles) is dissolved in 500 ml of pyridine. To the resultant solution triethylamine (10.5 g) is added and hydrogen sulfide is bubbled through the solution for two hours. The mixture is stirred for 18 hours at room temperature, evaporated to dryness and the residue is dissolved in chloroform. The chloroform solution is rinsed with water, dried, filtered and evaporated to dryness to yield a gum. A layer of ether is added on top of the gum and the mixture is allowed to crystallize at room temperature for 48 hours. The solid is filtered, rinsed with ether and dried in the air to give D,L-N-formyl-α-methyl-3-thiocarbamoylphenylalanine methyl ester, (24.6 g, 87%) m.p. 148°–150°.

C.

D,L-3-(4,5-Dihydro-4-hydroxy-4-trifluoromethylthiazol-2-yl)-N-formyl-α-methylphenylalanine methyl ester Starting with 5 g (17.8 mmoles) of D,L-N-formyl-α-methyl-3-thiocarbamoylphenylalanine methyl ester and proceeding according to step A of Example 13, there is obtained 4.97 g (72%) of D,L-3-(4,5-dihydro-4-hydroxy-4-trifluoromethylthiazol-2-yl)-N-formyl-α-methylphenylalanine methyl ester, m.p. 137°–139°.

D.

D,L-α-Methyl-3-(4-trifluoromethylthiazol-2-yl)phenylalanine hydrochloride

Starting with 3.82 g (9.80 mmoles) of D,L-3-(4,5-dihydro-4-hydroxy-4-trifluoromethylthiazol-2-yl)-N-formyl-α-methylphenylalanine methyl ester and carrying out a hydrolysis as in Example 14, there is obtained 3.43 g (96%) of D,L-α-methyl-3-(4-trifluoromethylthiazol-2-yl)-phenylalanine hydrochloride, m.p. 230° (dec.).

EXAMPLE 16

D,L-4-(Imidazol-2-yl)-α-methylphenylalanine dihydrochloride

A.

D,L-N-formyl-α-methyl-4-(methylthiocarboximidato)-phenylalanine methyl ester

D,L-N-Formyl-α-methyl-4-thiocarbamoylphenylalanine methyl ester (4.0 g, 14.3 mmoles) from step C of Example 3 is dissolved in 120 ml of acetone. Methylfluorosulfonate (1.6 g, 14.25 mmoles) is added and the mixture is stirred at room temperature for 18 hours. The solution is evaporated to dryness and the residue is partitoned between water and ethyl acetate. The aqueous layer is extracted twice with 50 ml of ethyl acetate. The aqueous extract is basified with sodium bicarbonate and extracted with ethyl acetate. The ethyl acetate extracts are combined, dried, filtered and evaporated to dryness to yield D,L-N-formyl-α-methyl-4-(methylthiocarboximidato)phenylalanine methyl ester, (3 g, 71%), m.p. 119°–120°.

B. D,L-4-(Imidazol-2-yl)-α-methylphenylalanine dihydrochloride hemihydrate

A mixture of 6.5 g (22 mmoles) of D,L-N-formyl-α-methyl-4-(methylthiocarboximidato)phenylalanine methyl ester, 2.0 g (22 mmoles) of oxalic acid and 3.0 g (22.5 mmoles) of aminoacetaldehyde diethyl acetate in 150 ml of methanol is stirred at 25° for 18 hours. The reaction mixture is evaporated to dryness and the residue dissolved in 100 ml of water. The aqueous solution is extracted with 50 ml of ethyl acetate which is discarded, made basic with solid sodium bicarbonate and extracted with 2 × 100 ml of ether which is discarded. The aqueous solution is then evaporated to dryness to leave a gummy residue which is stirred with 500 ml of chloroform for 24 hours. The chloroform solution is filtered to separate inorganic salts, dried and evaporated to leave an oil which is dissolved in 80 ml of concentrated hydrochloric acid. The solution is treated at 50° for 30 minutes, then heated to reflux for 4 hours. Cooling and filtering of the precipitated solid yields 2.1 g of D,L-4-(imidazol-2-yl)-α-methylphenylalanine dihydrochloride hemihydrate, m.p. 225°–230°. Concentration of the filtrate yields a further 0.88 g of product, bringing the yield to 42%.

EXAMPLE 17

D,L-4-(4,5-Dihydroimidazol-2-yl)-α-methylphenylalanine hydrochloride tetrahydrate A mixture of 3.5 g (11.9 mmoles) of D,L-N-formyl-α-methyl-4-(methylthiocarboximidato)phenylalanine methyl ester (prepared as in step A of Example 16 and 2.6 g (12.7 mmoles) of 2-bromoethylamine hydrobromide in 100 ml of methanol is stirred at 25° for 23 hours, after which the solvent is evaporated. The residue is redissolved in 100 ml of methanol and 10 g of AG$^R$ 1-X8 resin, in the hydroxide form, is added and the mixture stirred at 25° for 4 hours. The reaction mixture is filtered and the filtrate, upon evaporation to dryness, yields 3.2 g of a hygroscopic solid. The solid is dissolved in 50 ml of concentrated hydrochloric acid and the solution heated to reflux for 1 hour. The solution is evaporated and the residue redissolved in 50 ml of H$_2$O, the solution stirred with 0.5 g of charcoal for 30 minutes at 25°, filtered and evaporated to leave a thick syrup which crystallizes over 24 hours. This solid is slurried with 100 ml of ether and filtered to yield 2.76 g (59%) of D,L-4-(4,5-dihydroimidazol-2-yl)-α-methylphenylalanine dihydrochloride tetrahydrate, m.p. 145°–148° (dec.).

EXAMPLE 18

D,L-3-(Imidazol-2-yl)-α-methylphenylalanine dihydrochloride hydrate

A.

D,L-N-Formyl-α-methyl-3-(methylthiocarboximidato)-phenylalanine methyl ester

D,L-N-Formyl-α-methyl-3-thiocarbamoylphenylalanine methyl ester (4 g, 14.25 mmoles) from step B of Example 15 is dissolved in 120 ml of acetone. Methylfluoro sulfonate (1.6 g, 14.25 mmoles) is added and the mixture is stirred at room temperature for 18 hours. The solution is evaporated to dryness, the residue is partitioned between water and ethyl acetate. The aqueous layer is extracted twice with 50 ml of ethyl acetate. The aqueous extract is basified with sodium bicarbonate and extracted with ethyl acetate. The ethyl acetate extracts are combined, dried, filtered and evaporated to dryness to yield D,L-N-formyl-α-methyl-3-(thiomethylcarboximidato)phenylalanine methyl ester, (4.1 g, 97.5%), m.p. 115°–117°.

B. D,L-3-(Imidazol-2-yl)-α-methylphenylalanine dihydrochloride hydrate

Starting with 9.0 g (30.6 mmoles) of D,L-N-formyl-α-methyl-3-(methylthiocarboximidato)phenylalanine methyl ester and proceeding as in step B of Example 16, followed by recrystallization from 50 ml of water, there is obtained 2.0 g (19%) of D,L-3-(imidazole-2-yl)-α-methylphenylalanine dihydrochloride hydrate, m.p. 295°–298°.

EXAMPLE 19

D,L-3-(4,5-Dihydroimidazole-2-yl)-α-methylphenylalanine

A. hydrate

Starting with 5.0 g (17 mmoles) of D,L,N-formyl-α-methyl-3-(methylthiocarboximadato)phenylalanine methyl ester (prepared as in step A of Example 18) and proceeding as in Example 17, there is obtained 4.23 g (74%) of D,L-3-(4,5-dihydroimidazol-2-yl)-α-methylphenylalanine dihydrochloride hydrate, m.p. 308°–315° (dec.).

EXAMPLE 20

D,L-4-(Imidazol-2-yl)phenylalanine Dihydrochloride Hydrate

A. N-Acetyl-4-cyano-α-(ethoxycarbonyl)phenylalanine ethyl ester

To 50 ml of dimethylformamide is added 5.7 g (51 mmoles) of potassium tert-butoxide and 11.1 g (51 mmoles) of diethyl acetamidomalonate and the resulting mixture stirred at 25° for 15 minutes. The solution is then cooled to 10° and a solution of 10.0 g (51 mmoles) of 4-cyanobenzyl bromide, Case, J. Am. Chem. Soc., 47, 1143, (1925) in 40 ml of dimethylformamide is added dropwise over 20 minutes. The mixture is then stirred at 25° for 1 hour after which a further 0.285 g (2.5 mmoles) of potassium tert-butoxide and 0.55 (2.5 mmoles) of diethyl acetamidomalonate are added and stirring continued for 1 hour at 25°. The reaction mixture is then poured into 300 ml of ice water, causing the product to precipitate. Filtration, washing with water and drying yields 10.3 g (31 mmoles, 61%) of N-acetyl-4-cyano-α-(ethoxycarbonyl)phenylalanine ethyl ester, m.p. 160°–163°.

B. N-acetyl-α-ethoxycarbonyl-4-thiocarbamoylphenylalanine ethyl ester

Into a solution of 10.0 g (30 mmoles) of N-acetyl-4-cyano-α-(ethoxycarbonyl)phenylalanine ethyl ester and 3.5 g (35 mmoles) of triethylamine in 250 ml of pyridine, hydrogen sulfide gas is introduced until the solution is saturated. The reaction mixture is then stirred at 25° for 18 hours, followed by evaporation of the solvent. The residue is slurried with 50 ml of carbon disulfide for 1 hour and the resulting crystalline solid recovered by filtration to yield 8.7 g (24 mmoles, 80%) of N-acetyl-α-ethoxycarbonyl-4-thiocarbamoylphenylalanine ethyl ester, m.p. 168–172°.

C. N-acetyl-α-ethoxycarbonyl-4-(thiomethylcarboximidato)phenylalanine ethyl ester To a solution of 8.7 g (24 mmoles) of N-acetyl-α-ethoxycarbonyl-4-thiocarbamoylphenylalanine ethyl ester in 150 ml of acetone is added 1.7 ml (21 mmoles) of methyl fluorosulfonate and the resulting mixture stirred at 25° for 20 minutes. The reaction mixture, containing some precipitate, is then evaporated to dryness and 150 ml of water are added to the residue. This mixture is extracted with 100 ml of ethyl acetate, the aqueous phase made basic with solid sodium bicarbonate and extracted again with 2 × 100 ml of ethyl acetate. These second ethyl acetate extracts are dried, the solvent evaporated and the residue triturated with 20 ml of ether. The resulting solid is filtered to yield 5.15 g (13.5 mmoles, 56%) of N-acetyl-α-ethoxycarbonyl-4-(thiomethylcarboximidato)phenylalanine ethyl ester, m.p. 148°–149°. A further 1.15 g (3 mmoles, 12.5%) of product is recovered from the first ethyl acetate extract.

D. D,L-4-(Imidazol-2-yl)phenylalanine dihydrochloride hydrate

Starting with 6.1 g (16 mmoles) of N-acetyl-α-ethoxycarbonyl-4-(thiomethylcarboximidato)phenylalanine ethyl ester and following the procedure of step B of Example 16, there is obtained 1.65 g (5.1 mmoles, 32%) of D,L-4-(imidazol-2-yl)phenylalanine dihydrochloride hydrate, m.p. 120°–140° (dec.).

EXAMPLE 21

D,L-4-(4,5-dihydroimidazol-2-yl)phenylalanine dihydrochloride

Starting with 5.0 g (13.1 mmoles) of N-acetyl-α-ethoxycarbonyl-4-(thiomethylcarboximidato)-phenylalanine ethyl ester (from step C of Example 20) and following the procedure of Example 17, there is obtained 2.45 g (8 mmoles, 61%) of D,L-4-(4,5-dihydroimidazol-2-yl)phenylalanine dihydrochloride, m.p. 240°–245° (dec.).

EXAMPLE 22

D,L-3-(Imidazol-2-yl)phenylalanine dihydrochloride hydrate

Substituting 19.6 g (100 mmoles) of 3-cyanobenzyl bromide for 4-cyanobenzylbromide and following the procedure of steps A, B and C of Example 20 and step B of Example 16, there is obtained 7.08 g (22 mmoles, 22%) of D,L-3-(imidazol-2-yl)phenylalanine dihydrochloride hydrate, m.p. 250°–255°.

EXAMPLE 23

D,L-3-(2,3-Dihydro-1H-indol-5-yl)-α-methylalanine

A. 1-Benzoyl-5-chloromethyl-2,3-dihydro-1H-indole

1-Benzoyl-2,3-dihydro-1H-indole (Beilstein, 20, 257) (5.58 g, 25 mmole) is dissolved in 50 ml of glacial acetix acid, then 56 ml (ca 70 mmoles) of 40% formaldehyde are added, and dry hydrogen chloride passed into the solution which is maintained at 70° for 3 hours. The solution is evaporated, and the residue dissolved in benzene, and again evaporated to dryness to give 6.53 g of crude product. This residue is treated with carbon tetrachloride-hexane to give 4.05 g (60%) of 1-benzoyl-5-chloromethyl-2,3-dihydro-1H-indole, m.p. 107.5°–110.0°.

B. D.L-3-(2,3-dihydro-1H-indol-5-yl)-α-methylalanine

1-Benzoyl-5-chloromethyl-2,3-dihydro-1H-indole (14.85 g, 54.65 mmoles) and 6.95 g (54.65 mmoles) of ethyl 2-isocyanopropionate are dissolved in 100 ml of dimethylformamide. Then 7.72 g (60 mmole) of potassium tertiarybutoxide is added in three equal portions during a period of ten minutes. The internal temperature rises from 16° to 23° even with external cooling. The mixture is stirred for 0.5 hour, diluted with water, and extracted with diethyl ether. The combined ethereal extracts are washed, dried over magnesium sulfate, and evaporated to give 13.3 g (67.2%) of D,L-3-(1-benzoyl-2,3-dihydro-1H-indole-5-yl)-2-isocyano-2-methylpropionic acid ethyl ester, as a light red-brown oil which is suitable for the following procedure.

D,L-3-(1-benzoyl-2,3-dihydro-1H-indol-5-yl)-2-isocyano-2-methylpropionic acid ethyl ester (13.3 g, 36.4 mmoles) is treated with 100 g of ice, then 250 ml of concentrated hydrochloric acid is added, and the solution refluxed for a period of six hours. The mixture is refrigerated, and the solids collected to give 3.93 g of benzoic acid. The filtrate is evaporated to a small volume, then the pH adjusted to 10 with 15% ammonium hydroxide, the solution evaporated, and the residue dissolved in water. The aqueous solution is passed through an ion exchange column packed with Dowex 50W-X8 cation exchange resin and the product eluted with 1N aqueous ammonia solution. The resulting solids after evaporation of the aqueous ammonia solution are triturated with ethanol to give 4.26 g (52.7%) of D,L-3-(2,3-dihydro-1H-indol-5-yl)-α-methylalanine, m.p. 264°-268° (dec.).

EXAMPLE 24

D,L-α-Methyl-3-(1H-2-oxindol-5-yl)alanine

A.

D.L-3-(1-Benzoyl-2,3-dihydro-1H-indol-5-yl)-2-isocyano 2-methylpropionic acid methyl ester Methyl 2-isocyanopropionate (9.4 g, 83 mmoles) is added with cooling to a cold solution of 4.5 g (83 mmoles) of sodium methylate in 50 ml of dimethylformamide. The solution is added during the course of 10 minutes to a solution of 14.9 g (55 mmole) of 1-benzoyl-5-chloromethyl-2,3-dihydro-1H-indole (from step A of Example 23) in 50 ml of dimethylformamide maintained at 0°-12°. The mixture is stirred for 0.5 hour, then poured into 1000 ml of ice water, the solids collected, and dried to give 16.1 g (84% of crude product. The crude product is crystallized from ethyl acetate to give D,L-3-(1-benzoyl-2,3-dihydro-1H-indol-5-yl)-2-isocyano-2-methylpropionic acid methyl ester, m.p. 148°-150°.

B.

D,L-3-(1-Benzoyl-2,3-dihydro-1H-indol-5-yl)-N-formyl-α-methylalanine methyl ester D,L-3-(1-Benzoyl-2,3-dihydro-1H-indol-5-yl)-2-isocyano-2-methyl propionic acid methyl ester (348 mg, 1mmole) is stirred for 0.5 hour under $N_2$ in a solution of 11 ml of ethyl acetate containing three drops of concentrated hydrochloric acid. The mixture is extracted with water, the ethyl acetate layer dried over magnesium sulfate, filtered, and evaporated to give 365 mg of crude product. The residue is crystallized from a mixture of chloroform and ethyl acetate to give 291 mg (79.4%) of D,L-3-(1-benzoyl-2,3-dihydro-1H-indol-5-yl)-N-formyl-α-methylalanine methyl ester, m.p. 163°-166°.

C.

D,L-3-(1-benzoyl-1H-indol-5-yl)-N-formyl-α-methylalanine methyl ester

D,L-3-(1-benzoyl-1H-indol-5-yl)-N-formyl-α-methyl-alanine methyl ester (8.1 g, 22 mmoles) is dissolved in 400 ml of chloroform, the solution cooled to 40°, then 7.5 g (33 mmoles) of 2,3-dichloro-5,6-dicyano-1,4-benzoquinone (DDQ) added and the solution is refluxed for three hours under $N_2$. The solution is cooled, diluted with 200 ml of chloroform, the chloroform solution extracted with 3 × 10 ml of 5% sodium carbonate solution, the combined chloroform extracts washed with water, dried over magnesium sulfate, filtered, and evaporated to give a solid residue. The solid is crystallized from ethyl acetate-diethyl ether to give 6.24 g (77.8%) of D,L-3-(1-benzoyl-1H-indol-5-yl)-N-formyl-α-methylalanine methyl ester, m.p. 111°-115°.

D.

D,L-3-(1-benzoyl-3-bromo-1H-indol-5-yl)-N-formyl-α-methylalanine methyl ester

D,L-3-(1-benzoyl-1H-indol-5-yl)-N-formyl-α-methylalanine methyl ester (6.56 g, 18 mmoles) is dissolved in 55 ml of chloroform, then 2.96 g (18.5 mmoles) of bromine in 50 ml of chloroform are added during a period of ten minutes accompanied by a small rise in internal temperature. The solution is left 15 minutes at room temperature, then extracted with water, the combined chloroform extracts dried over magnesium sulfate, and evaporated to give 9 g of solids. The solids are triturated with about 100 ml of diethyl ether to give 7.37 g (92.4%) of D,L-3-(1-benzoyl-3-bromo-1H-indol-5-yl)-N-formyl-α-methylalanine methyl ester, m.p. 183°-185°.

E. D,L-α-methyl-3-(1H-2-oxindol-5-yl)-alanine

D,L-3-(1-benzoyl-3-bromo-1H-indol-5-yl)-N-formyl-α-methylalanine methyl ester (6.21 g, 14 mmoles) is suspended in a mixture of 200 ml of methanol, 40 ml of concentrated hydrochloric acid, and 80 ml of water and heated for 3 hours at 80°. The methanol is removed in vacuo, 120 ml of concentrated hydrochloric acid added and the solution heated for a further 8.5 hours. The solution is evaporated in vacuo. The residue is dissolved in water and evaporated several times. Ammonium hydroxide is added, the solution evaporated, and the residue triturated with ethanol to give 4.7 g of solids. The solids are crystallized from ethanol-water to give 1.1 g (28.5%) of D,L-α-methyl-3-(1H-2-oxindol-5-yl)alanine, m.p. 300° (dec.).

EXAMPLE 25

D,L-3-(1H-indol-5-yl)-α-methylalanine

D,L-3-(1-benzoyl-1H-indol-5-yl)-N-formyl-α-methylalanine methyl ester (3.2 g, 8.8 mmoles) (from step C of Example 24) is refluxed 6 hours under $N_2$ in 45 ml of methanol and 32 ml 2N sodium hydroxide solution. The methanol is removed in vacuo, 2N hydrochloric acid is added to the cooled basic solution until the pH is adjusted to 3.4. The solution is extracted with diethyl ether to remove benzoic acid. The aqueous acid solution is treated with ammonium hydroxide to give a pH of 10, the mixture refrigerated, the solids collected, washed, and dried to give 1.2 g (63%) of D,L-3-(1H-indol-5-yl)-α-methylalanine, m.p. 283°-285° (dec.).

EXAMPLE 26

D,L-3-(Benzimidazol-2-thione-5-yl)-2-methylalanine hydrate

A.

D,L-N-Formyl-α-methyl-4-formylamino-3-nitrophenylalanine methyl ester

D,L-N-Formyl-α-methyl-4-aminophenylalanine methyl ester, 91.4 g, 387 mmoles, (from step C of Example 11) is added to 500 ml of benzene. Formic-acetic anhydride (50% excess) is added and the mixture refluxed for 30 minutes. The resulting solution is washed with 1N aqueous sodium carbonate until the washes remain basic. The benzene solution is then dried (MgSO$_4$) and evaporated to give 80.3 g of D,L-N-formyl-α-methyl-4-formylaminophenylalanine methyl ester as an oil. Nitration as in step B of Example 11 of this oil affords 63.5 g of D,L-N-formyl-α-methyl-4-formylamino-3-nitrophenylalanine methyl ester, m.p. 177°–179°.

B.

D,L-N-Formyl-α-methyl-4-amino-3-nitrophenylalanine methyl ester

D,L-N-formyl-α-methyl-4-formylamino-3-nitrophenyl-alanine methyl ester (15 g, 48.5 mmoles) is treated according to the procedure of step A of Example 9. There is obtained 13.6 g (100%) of D,L-N-formyl-α-methyl-4-amino-3-nitro-phenylalanine methyl ester, m.p. 133°–136°.

C. D,L-3,4-Diamino-N-formyl-α-methylphenylalanine methyl ester

A mixture of 3.0 g (10.7 mmoles) of D,L-N-formyl-α-methyl-4-amino-3-nitrophenylalanine methyl ester and 100 ml of methanol is hydrogenated over 0.20 g of 10% pd on charcoal under 18.2 kg of hydrogen pressure for 30 minutes. The reaction mixture is filtered, the filtered solution evaporated to dryness, 50 ml of benzene is added and re-evaporated and the residue triturated with 25 ml of ether. The resulting solid is filtered to yield 2.5 g (94%) of D,L-3,4-diamino-N-formyl-α-methylphenylalanine methyl ester, m.p. 118°–120°.

D. D,L-3-(Benzimidazol-2-thione-5-yl)-2-methylalanine hydrate

To a solution of 6 grams (24 mmoles) of D,L-3,4-diamino-N-formyl-α-methylphenylalanine methyl ester in 100 ml of methanol is added 5.4 grams (72 mmoles) of carbon disulfide and 4.0 g (72 mmoles) of potassium hydroxide pellets dissolved in 15 ml of water. The reaction mixture is refluxed for 2 hours and then evaporated to remove the methanol. 50 ml of water are then added to the residue followed by 5 ml of acetic acid. The precipitate is filtered and washed with water. The crude D,L-3-(Benzimidazol-2-thione-5-yl)-N-formyl-α-methylalanine methyl ester is heated with 200 ml of 6N HCl for 3 hours on a steam bath. The solution is evaporated and the residue taken up in 50 ml of water. The solution is basified with ammonium hydroxide, evaporated to dryness and then boiled in water. The product is filtered and dried at 100°. Yield, 2.2 g (33%), m.p. 280° (dec.).

EXAMPLE 27

D,L-3-(2-Aminobenzimidazol-5-yl)-2-methylalanine dihydrochloride

A. D,L-N-acetyl-3,4-diamino-α-methylphenylalanine methyl ester

A suspension of 10.0 g (34 mmoles) of D,L-N-acetyl-4-amino-α-methyl-3-nitrophenylalanine methyl ester (prepared as in step A of Example 9) and 1.0 g of 10% Pd on charcoal in 300 ml of methanol is shaken under hydrogen at 18.2 kg pressure until hydrogenation is complete (30 minutes). The reaction mixture is filtered, evaporated to dryness, the residue slurried with 50 ml ethyl acetate and again evaporated. The resulting solid is slurried well with 100 ml of ether and filtered to yield 7.87 g (87%) of D,L-N-acetyl-3,4-diamino-α-methylphenylalanine methyl ester, m.p. 136°–139°.

B. D,L-3-(2-aminobenzimidazol-5-yl)-2-methylalanine dihydrochloride

To a mixture of 1.0 g (3.8 mmoles) of D,L-N-acetyl-3,4-diamino-α-methylphenylalanine methyl ester and 30 ml of water is added 1.0 g (9.5 mmoles) of cyanogen bromide in two equal portions at 30 minute intervals. The reaction mixture is stirred for 1 hour at 25° and then extracted with 2 × 50 ml of ethyl acetate, which is discarded. The aqueous phase is evaporated to dryness and the residue dissolved in 20 ml of concentrated hydrochloric acid. The resulting solution is refluxed for one hour, cooled and the resulting precipitate filtered, washed well with ethanol and ether to yield 0.64 g (55%) of D,L-3-(2-aminobenzimidazol-5-yl)-2-methylalanine dihydrochloride, m.p. 300°–305° (dec.).

EXAMPLE 28

D,L-2-Methyl-3-(benzoxazol-2-on-6-yl)alanine hydrochloride

A. D,L-3-Hydroxy-4-nitro-α-methylphenylalanine hydrochloride

D,L-N-formyl-3-hydroxy-α-methyl-4-nitrophenylalanine methyl ester prepared as in step A of Example 7 (2.8 g, 10 mmoles) in concentrated hydrochloric acid (20 ml) is heated on a steam bath for 8 hours. The reaction mixture is concentrated to a small volume and the solid is filtered to yield 2.54 g (92%) of D,L-3-hydroxy-4-nitro-α-methylphenylalanine hydrochloride, m.p. 239°–243° (dec.).

B. D,L-3-Hydroxy-4-amino-α-methylphenylalanine dihydrochloride

D,L-3-Hydroxy-4-nitro-α-methylphenylalanine hydrochloride (2.8 g, 10 mmoles) in a mixture of ethanol (25 ml) and 5% hydrochloric acid (25 ml) is reduced by hydrogen gas in a Parr hydrogenator over 5% palladium on charcoal. The absorption of hydrogen is over within 5 minutes. Evaporation of the solvent under vacuum leaves 2.2 g (78%) of D,L-3-hydroxy-4-amino-α-methylphenylalanine dihydrochloride as a white solid, m.p. 210° (dec.).

C. D,L-2-Methyl-3-benzoxazol-2-on-6-yl)alanine hydrochloride

D,L-3-Hydroxy-4-amino-α-methylphenylalanine dihydrochloride (0.92 g, 3.2 mmoles) is dissolved in water (15 ml) and phosgene is bubbled through the solution, keeping the temperature between 50° and 60° for 20 minutes. A white solid precipitates from the solution during the reaction. It is filtered and air-dried to yield 350 mg (40%) of D,L-2-methyl-3-(benzoxazol-2-on-6-yl)alanine hydrochloride, m.p. 285° (dec.).

The filtrate contains D,L-3-hydroxy-4-amino-α-methylphenylalanine dihydrochloride which is recycled to yield an additional 454 mg of the title compound. The overall yield is 91%, m.p. 285° (dec.).

EXAMPLE 29

D,L-3-(2-Aminobenzothiazol-6-yl)-2-methylalanine dihydrochloride

A. D,L-N-Acetyl-3-(2-aminobenzothiazol-6-yl)-2-methylalanine methyl ester

To a mixture of 5.0 g (20 mmoles) of D,L-N-acetyl-4-amino-α-methylphenylalanine methyl ester (prepared as in step A of Example 5) and 3.56 g (44 mmoles) of sodium thiocyanate in 50 ml of acetic acid, cooled to 10°, is added a solution of 3.52 g (22 mmoles) of bromine in 10 ml of acetic acid over a 15 minute period. The reaction mixture is then stirred at 25° for 2 hours and the inorganic salts which precipitate are removed by filtration. The filtrate is evaporated to dryness and the residue partitioned between 150 ml of water and 150 ml of ethyl acetate.

The aqueous solution is basified with solid sodium hydroxide (pH>10) and extracted with 100 ml of ethyl acetate. During the extraction, crystals begin to separate from the organic layer which upon filtration yields 2.58 g (8.4 mmoles, 42%) of D,L-N-acetyl-3-(2-aminobenzothiazol-6-yl)-2-methylalanine methyl ester, m.p. 228°-229°.

B. D,L-3-(2-aminobenzothiazol-6-yl)-2-methylalanine dihydrochloride

A mixture of 2.58 g (8.4 mmoles) of D,L-N-acetyl-3-(2-aminobenzothiazol-6-yl)-2-methylalanine methyl ester and 60 ml of concentrated hydrochloric acid is heated to reflux for 1.5 hours, cooled in the refrigerator, and the precipitated solid filtered to yield 1.91 g (5.9 mmoles, 70%) of D,L-3-(2-aminobenzothiazol-6-yl)-2-methylalanine dihydrochloride, m.p. 315°-320° (dec.).

EXAMPLE 30

D,L-3-(2-Aminobenzothiazol-6-yl)alanine dihydrochloride

A. D,L-N-Formyl-4-nitrophenylalanine methyl ester

Starting with 45 g (0.217 mole) of D,L-N-formylphenylalanine methyl ester [G. E. Hein, et al., J. Am. Chem. Soc., 84, 4487 (1962)] and carrying out a nitration as in step B of Example 11, there is obtained 42.0 g (77%) of D,L-N-formyl-4-nitrophenylalanine methyl ester, m.p. 99°-100° of a sample recrystallized from ethanol.

B. D,L-3-(2-Aminobenzothiazol-6-yl)-N-formylalanine methyl ester

Starting with 9.3 g (42 mmoles) of D,L-4-amino-N-formylphenylalanine methyl ester (prepared by catalytic hydrogenation of 10.6 g (42 mmoles) of D,L-N-formyl-4-nitrophenylalanine methyl ester in 100 ml of methanol over 1.0 g of 10% Pd on charcoal under 18.2 kg hydrogen pressure for 1 hour, filtration and evaporation of the filtrate to dryness) and proceeding as in step A of Example 29, there is obtained 3.1 g (26%) of D,L-3-(2-aminobenzothiazol-6-yl)-N-formyl alanine methyl ester, m.p. 166°-169°.

C. D,L-3-(2-aminobenzothiazol-6-yl)alanine dihydrochloride

A mixture of 3.1 g (11.1 mmoles) of D,L-3-(2-aminobenzothiazol-6-yl)-N-formylalanine methyl ester and 40 ml of concentrated hydrochloric acid is heated to reflux for 1.5 hours, cooled in an ice bath and the precipitate filtered and dried to yield 3.0 g (87%) of D,L-3-(2-aminobenzothiazol-6-yl)-alanine dihydrochloride, m.p. 295°-300° (dec.).

EXAMPLE 31

D,L-2-Methyl-3-(2,1,3-benzothiadiazol-5-yl)-alanine hydrochloride

A solution of 2.9 gm (11 mmoles) of N-acetyl-3,4-diamino-α-methylphenylalanine methyl ester (prepared as in step A of Example 27) and 5.0 ml of thionyl aniline in 120 ml of pyridine is heated to reflux for 5 hours. The solution is evaporated to dryness, treated with a mixture of water and methanol and evaporated, the solid washed with 50 ml of 1N hydrochloric acid and water and dried. The resulting solid is slurried with a small amount of ether and filtered to yield 2.31 g of D,L-N-acetyl-3-(2,1,3-benzothiadiazol-5-yl)-2-methylalanine methyl ester.

A mixture of 2.31 g (7.9 mmoles) of N-acetyl-3-(2,1,3-benzothiadiazoly-5-yl)-2-methylalanine methyl ester and 50 ml of 12N hydrochloric acid is heated to reflux for 1 hour, evaporated to dryness, redissolved in water and re-evaporated to dryness. The residue is slurried with isopropanol and filtered to yield 1.7 g (57%) of 3-(2,1,3-benzothiadizol-5-yl)-2-methylalanine hydrochloride, m.p. 272°-274° (dec.).

EXAMPLE 32

D,L-3-(1,3-Dihydrobenzo-2,1,3-thiadiazol-5-yl)-2-methylalanine 2,2-dioxide hydrate A mixture of 7.5 g (24 mmoles) of D,L-3-(1,3-dihydrobenzo-2,1,3-thiadiazol-5-yl)-N-formyl-2-methylalanine 2,2-dioxide methyl ester (prepared as in step A of Example 33) and 5 g of sodium hydroxide in 100 ml of water is heated to reflux under an atmosphere of nitrogen for 1 hour. The reaction mixture is then cooled, made acidic with 6N hydrochloric acid and sufficient concentrated ammonium hydroxide is added to make it basic. The solution is evaporated to dryness, redissolved in a minimum of water and the solution passed through an acid resin (Dowex 50WX8). The product is eluted from the resin with 1N ammonium hydroxide, which upon evaporation and trituration of the residue with ethanol, gives 5.05 g (73%) of D,L-3-(1,3-dihydrobenzo-2,1,3-thiadiazol-5-yl)-2-methylalanine-2,2-dioxide hydrate, m.p. 234°-236°.

EXAMPLE 33

D,L-3-(1,3-Dihydrobenzo-2,1,3-thiadiazol-5-yl)-2-methylalanine 2,2-dioxide methyl ester hydrochloride A. D,L-3-(1,3-Dihydrobenzo-2,1,3-thiadiazol-5-yl)-N-formyl-2-methylalanine 2,2-dioxide methyl ester To 30 ml of refluxing diglyme is added 560 mg (5.8 mmoles) of sulfamide in 15 ml of diglyme, followed immediately by addition of 1.4 g (5.6 mmoles) of D,L-

3,4-diamino-N-formyl-α-methylphenylalanine methyl ester (prepared as in step C of Example 26). Refluxing is continued for 30 minutes, the solvent is evaporated and the residue dissolved in ethyl acetate. The ethyl acetate solution is washed with water and then with 5% sodium bicarbonate solution. The bicarbonate solution is then acidified with hydrochloric acid, extrcted with ethyl acetate, the organic extracts dried and evaporated. Trituration with chloroform of the residue gives the crystalline product, 0.70 g (40%), m.p. 175°–178°.

D,L-3-(1,3-Dihydrobenzo-2,1,3-thiadiazol-5-yl)-2-methylalanine 2,2-dioxide methyl ester hydrochloride To a solution of 2.0 g (6.4 mmoles) of D,L-3-(1,3-dihydrobenzo-2,1,3-thiadiazol-5-yl)-N-formyl-2-methylalanine 2,2-dioxide methyl ester in 100 ml of methanol is added 5 drops of concentrated hydrochloric acid and the solution left at 25°. The addition of acid is repeated every two days over a period of two weeks after which time the solvent is evaporated and the residue is refluxed in 50 ml of toluene for 20 hours to remove residual methanol. Filtration and drying yields 1.76 g (85%) of D,L-3-(1,3-dihydrobenzo-2,1,3-thiadiazol-5-yl)-2-methylalanine 2,2-dioxide methyl ester hydrochloride, m.p. broad 145°–165° (dec.).

EXAMPLE 34

D,L-3-(1,3-Dihydrobenzo-2,1,3,-thiadiazol-5-yl)-alanine 5,5-dioxide hydrate

A. D,L-4-Formamido-N-formylphenylalanine methyl ester

Starting with 42 g (0.167 moles) of D,L-N-formyl-4-nitrophenylalanine methyl ester (prepared as in step A of Example 30) and hydrogenating as in step C of Example 11 and formylating as in step A of Example 26, there is obtained 19.8 g (47%) of D,L-4-formamido-N-formylphenylalanine methyl ester, m.p. 105°–107°.

B. D,L-4-Formamido-N-formyl-3-nitrophenylalanine methyl ester

Starting with 18.0 g (72 mmoles) of D,L-4-formamido N-formylphenylalanine methyl ester and carrying out a nitration according to step A of Example 26, there is obtained 18.0 g (85%) of D,L-4-formamido-N-formyl-3-nitrophenylalanine methyl ester, m.p. 140°–141° of a sample recrystallized from methanol.

C. D,L-4-Amino-N-formyl-3-nitrophenylalanine methyl ester

Starting with 13.0 gm (44 mmoles) of D,L-4-formamido-N-formyl-3-nitrophenylalanine methyl ester and carrying out a selective hydrolysis as in step A of Example 9, there is obtained 9.8 (83%) of D,L-4-amino-N-formyl-3-nitrophenylalanine methyl ester, m.p. 160°–163°.

D. D,L-3-(1,3-Dihydrobenzo-2,1,3-thiadiazol-5-yl)-N-formylalanine 2,2-dioxide methyl ester Starting with 9.7 g (36 mmoles) of D,L-4-amino-N-formyl-3-nitrophenylalanine methyl ester, and following the procedures of step C of Example 26, and step A of Example 33 there is obtained 4.0 g (37%) of D,L-3-(1,3-dihydrobenzo-2,1,3-thiadiazol-5-yl)-N-formylalanine 2,2-dioxide methyl ester, a sample of which when recrystallized from water, has m.p. 182°–185°.

E. D,L-3-(1,3-Dihydrobenzo-2,1,3-thiadiazol-5-yl)alanine 2,2-dioxide hydrate

Starting with 4.8 g (16 mmoles) of D,L-3-(1,3-dihydrobenzo-2,1,3-thiadiazol-5-yl)-N-formylalanine dioxide methyl ester and following the procedure of Example 32, there is obtained 3.72 g (84%) of D,L-3-(1,3-dihydrobenzo-2,1,3-thiadiazol-5-yl)-alanine 2,2-dioxide hydrate, m.p. 195°–225° (dec.).

EXAMPLE 35

D,L-3-(1,3-dihydro-1,3-dimethylbenzo-2,1,3-thiadiazol-5-yl)-2-methylalanine 2,2-dioxide hydrate A. D,L-3-(1,3-dihydro-1,3-dimethylbenzo-2,1,3-thiadiazol-5-yl)-N-formyl-2-methylalanine 2,2-dioxide methyl ester To a solution of 1.9 g (6.1 mmoles) of D,L-3-(1,3-dihydrobenzo-2,1,3-thiadiazol-5-yl)-N-formyl-2-methylalanine 2,2-dioxide methyl ester (prepared as in step A of Example 33) in 50 ml of methanol, is added in portions a solution of 4 g (95 mmoles) of diazomethane in 200 ml of ether. The solvents are evaporated, the residue dissolved in 150 ml of ethyl acetate, the organic solution washed with 5% sodium bicarborate solution, water, dried and evaporated. Recrystallization of the residue from ethanol gives 1.2 g c58%) of D,L-3-(1,3-dihydro-1,3-dimethylbenzo-2,1,3-thiadiazol-5-yl)-N-formyl-2-methyl alanine 2,2-dioxide methyl ester, m.p. 167°–168°.

B. D,L-3-(1,3-dihydro-1,3-dimethylbenzo-2,1,3-thiadiazol-5-yl)-2-methylalanine 2,2-dioxide hydrate A mixture of 1.0 g (2.9 mmoles) of D,L-3-(1,3-dihydro-1,3-dimethylbenzo-2,1,3-thiadiazol-5-yl)-N-formyl-2-methyl alanine 2,2-dioxide methyl ester, 0.50 g of sodium hydroxide and 6 ml of water is heated on the steam bath for 45 minutes. The reaction is cooled, acidified with 3N hydrochloric acid, rebasified with concentrated ammonium hydroxide and evaporated to dryness. Three successive portions of 25 ml of water are then evaporated from the residue and 25 ml of water added and the insoluble solid filtered to give 0.85 g (92%) of D,L-3-(1,3-dihydro-1,3-dihydro-1,3-dimethylbenzo-2,1,3-thiadiazol-5-yl)-2-methylalanine 2,2-dioxide hydrate, m.p. 250°–252° (dec.).

EXAMPLE 36

D,L-α-Methyl-3-[4-methyl-2(1H)-oxoquinolin-6-yl]alanine

A. D,L-N-acetyl-4-(3-oxobutanamido)-α-methylphenylalanine methyl ester

N-acetyl-4-amino-α-methylphenylalanine methyl ester (5.01 g, 20 mmole), prepared as in step A of Example 5, is suspended in 200 ml of dry benzene, then warmed 20 minutes on the steam bath with 8.72 g (30 mmoles) of 6-keto-2,2,4-trimethyl-1,3-dioxane (diketene acetone adduct) until solution results. The solution is heated on the steam bath for a further hour until solids appear in the solution. The mixture is evaporated to dryness in vacuo, the residue triturated with diethyl ether, and the solids collected to yield 6.53 g (97.3%) of D,L-N-acetyl-4-(3-oxobutanamido)-α-methyl-phenylalanine methyl ester, m.p. 183°–185°.

B.
D,L-N-Acetyl-α-methyl-3-[4-methyl-2(1H)-oxoquinolin-6-yl]alanine

D,L-N-acetyl-4-(3-oxobutanamido-α-methyl-phenylalanine methyl ester (6.53 g, 19.5 mmoles) is added portionwise to 15 ml of concentrated sulfuric acid and the solution heated slowly to 100° during 38 minutes. The solution is cooled to 60° and slowly poured into 400 ml of ice-water, the solids collected, and dried to give 4.1 (69.7%) of crude D,L-N-acetyl-α-methyl-3[4-methyl-2-(1H)-oxoquinolin-6-yl]alanine, m.p. 275°–278° (with gassing). The product is purified by solution in dilute sodium bicarbonate and extraction of the solution with ethyl acetate. The bicarbonate solution is acidified, the solids collected and dried to give 3 g (51%) of pure D,L-N-acetyl-α-methyl-3-[4-methyl-2(1H)oxoquinolin-6-yl)alanine, m.p. 284°–287° (gassing).

C.
D,L-α-Methyl-3-[4-methyl-2(1H)-oxoquinolin-6-yl]alanine

D,L-N-acetyl-α-methyl-3-[4-methyl-2(1H)-oxoquinolin-6-yl]alanine (3.02 g, 10 mmoles) is refluxed for 5 hours in 60 ml of concentrated hydrochloric acid and the solvent is removed in vacuo. The crude residue is dissolved in distilled water, the solution treated with ammonium hydroxide to give a pH of 10, and the solvent is removed in vacuo. The solid is triturated with distilled water to give 2.47 g (90.5%) of D,L-α-methyl-3-[4-methyl-2(1H)-oxoquinolin-6-yl]alanine, m.p. 259°–263° (dec).

EXAMPLE 37

D,L-3-[4-Methyl-2(1H)-oxoquinolin-6-yl]alanine

D,L-N-acetyl-4-(3-oxobutanamido)phenylalanine methyl ester

D,L-N-acetyl-4-aminophenylalanine methyl ester (5.91 g, 25 mmoles) [Chem. Abst., 54, 22673b, (1960) is warmed for twentyfive minutes on a steam bath with 10.9 g (37.5 mmoles) of 6-keto-2,2,4-trimethyl-1,3-dioxene in 200 ml of benzene (diketene acetone adduct), the crude product isolated and purified as in step A of Example 36 to give 8.0 g (99%) of D,L-N-acetyl-4-(3-oxobutanamido)phenylalanine methyl ester, m.p. 137.5°–139.0°.

B.
D,L-N-Acetyl-3-[4-methyl-2(1H)-oxoquinolin-6-yl]alanine

A mixture of 8 g (25 mmole) of D,L-N-acetyl-4-(3-oxobutanamido)phenylalanine methyl ester and 20 ml of concentrated sulfuric acid is heated for 93 minutes at 70°–90° and the product isolated as in step B of Example 36 to give 6.57 g (91.2%) of D,L-N-acetyl-3-[4-methyl-2-(1H)-oxoquinolin-6-yl]-alanine which is of suitable purity for hydrolysis.

C. D,L-3-[4-Methyl-2(1H)-oxoquinolin-6-yl]alanine hydrate

D,L-N-acetyl-3-[4-methyl-2(1H)-oxoquinolin-6-yl]alanine (5.3 g, 20 mmoles) is refluxed for 6 hours in 105 ml of concentrated hydrochloric acid. Working the reaction up according to the procedure of step C of Example 36 gives 4.1 g (82.8%) of D,L-3-[4-methyl-2(1H)-oxoquinolin-6-yl]alanine hydrate, m.p. 247°–249° (gassing).

EXAMPLE 38

D,L-2-Methyl-3-(quinoxalin-6-yl)alanine dihydrochloride

A. D,L-N-Formyl-2-methyl-3-(quinoxalin-6-yl)alanine methyl ester

A mixture of 10.0 g (35.6 mmoles) of D,L-4-amino-N-formyl-α-methyl-3-nitrophenylalanine methyl ester (prepared as in step B of Example 26) and 300 ml of methanol is hydrogenated over 1.0 g of 10% Pd on charcoal under 18.1 kg of hydrogen pressure for 1 hour. The reaction mixture is filtered and the filtrate evaporated to dryness. The residue is dissolved in 70 ml of hot water and to this solution is added a solution of 7.0 ml of 40% aqueous glyoxal (50 mmoles) and 8.0 g (77 mmoles) of sodium bisulfite in 50 ml of water. The resulting solution is heated on a steam bath for 25 minutes, cooled and basified with sodium carbonte. Filtration and drying of the resulting precipitate yields 7.9 g (81%) of D,L-N-formyl-2-methyl-3-(quinoxalin-6-yl)alanine methyl ester, m.p. 167°–168°.

D,L-2-Methyl-3-(quinoxalin-6-yl)alanine dihydrochloride

A mixture of 7.3 g (26.8 mmoles) of D,L-N-formyl-2-methyl-3-(quinoxalin-6-yl)alanine methyl ester and 70 ml of concentrated hydrochloric acid is heated to reflux for 1 hour. The solution is then evaporated to dryness, 50 ml of water-added and again evaporated to dryness. The residue is dissolved in 100 ml of water and decolorized by treating with 1 g of charcoal at 60° hour. The mixture is filtered, the filtrate evaporated to dryness and the residue slurried wth 50 ml of ethanol. Filtration of the resulting solid yields 5.57 g (68%) of D,L-2-methyl-3-(quinoxalin-6-yl) alanine dihydrochloride, m.p. 235°–250° (dec.).

EXAMPLE 39

D,L-2-Methyl-3-(2-hydroxyquinoxalin-6-yl)alanine and D,L-2-methyl-3-(2-hydroxyquinoxalin-7-yl)alanine A mixture of 5.0 g (17.8 mmoles) of D,L-4-amino-N-formyl-α-methyl-3-nitrophenylalanine methyl ester (prepared as in step B of Example 26) and 250 ml of methanol is hydrogenated over 0.30 g of 10% Pd on charcoal under 18.1 kg of hydrogen pressure for 45 minutes. The reaction mixture is filtered and the filtrate evaporated to dryness. The residue is dissolved in 50 ml of water and to this solution is added a solution of 4.1 g (39.4 mmoles) of sodium bisulfite and 1.8 g (24 mmoles) of glyoxalic acid in 20 ml of water and the whole is heated on the steam bath for 15 minutes. The reaction mixture is cooled and extracted once with 100 ml of ethyl acetate to remove impurities, basified with 5.0 g of sodium carbonate and extracted with 3 × 100 ml of ethyl acetate. The ethyl acetate extract is washed with 25 ml of water, dried and evaporated. The residue (2.7 g) is added to 40 ml concentrated hydrochloric acid and the mixture heated to reflux for 1 hour. The solution is evaporated to dryness and the residue decolorized by redissolving in 100 ml of water and warming at 60° for 1 hour with 0.5 g of charcoal. After filtration, the solution is made basic with concentrated ammonium hydroxide and evaporated to dryness. The residue is dissolved in a minimum of water and this solution passed through a strong acid resin (50W.X8). Elution with 1N ammonium hydroxide and evaporation gives a solid which is slurried with 20 ml of ethanol and filtered to yield 1.21 g (28%) of a mixture of D,L-2-methyl-3-[2-hydroxyquinoxalin-6-yl)alanine and D,L2-methyl-3-(2-hydroxyquinoxalin-7-yl)alanine, m.p. 220°–225° (dec.). Nuclear magnetic resonance spectroscopy indicates the two isomers to be present in approximately equal amounts.

EXAMPLE 40

D,L-3-(2,3-Dihydroxyquinoxalin-6-yl)-2-methylalanine hemihydrochloride

A.
D,L-3-(2,3-Dihydroxyquinoxalin-6-yl)-N-formyl-2-methyl alanine methyl ester A mixture of 5.0 g (20 mmoles) of D,L-3,4-diamino N-formyl-α-methylphenylalanine methyl ester (prepared as in step C of Example 26) and 60 ml of diethyloxalate is heated to reflux for 4 hours and filtered hot. The solid product thus filtered is washed with 50 ml of ether to yield 4.9 g (80%) of D, L-3-(2,3-dihydroxyquinoxalin-6-yl)-N-formyl-2-methylalanine methyl ester, m.p. 267°–269° (dec.).

B.
D,L-3-(2,3-Dihydroxyquinoxalin-6-yl)-2-methylalanine hemihydrochloride

A mixture of 3.0 g (10 mmoles) of D,L-3-(2,3-dihydroxyquinoxalin-6-yl)-N-formyl-2-methylalanine methyl ester and 60 ml of concentrated hydrochloric acid is heated to reflux for 90 minutes. The reaction mixture is evaporated to dryness, the residue taken up in 100 ml of water and decolorized by addition of 0.5 g charcoal and warming on the steam bath for 15 minutes, the mixture filtered and the filtrate evaporated to dryness. The residue is taken up in a minimum of warm water (about 10 ml) and upon cooling the product crystallizes. Filtration and drying yield 1.4 g (47%) of D,L-3-(2,3-dihydroxyquinoxalin-6-yl)-2-methylalanine hemihydrochloride, m.p. 280°–285° (dec.).

EXAMPLE 41

D,L-3-(Quinoxalin-6-yl)alanine dihydrochloride

A. D,L-4-Acetamido-N-acetylphenylalanine methyl ester

A solution of 89.5 g (0.38 mole) of D,L-N-acetyl4-aminophenylalanine methyl ester [Chem. Abst., 54, 22673b (1960)] in 680 ml of benzene and 100 ml of acetic anhydride is heated on the steam bath for 15 minutes and then left at 25° for 16 hours. The crystallized solid filtered, washed with 200 ml of ether and air dried to yield 98.5 g (93%) of D,L-4-acetamido-N-acetylphenylalanine methyl ester, m.p. 173°–175°.

B. D,L-4-acetamido-N-acetyl-3-nitrophenylalanine methyl ester

To 250 ml of 90% nitric acid cooled to −15° is added 98.5 g (0.35 mole) of D,L-4-acetamido-N-acetylphenylalanine methyl ester with stirring over a period of 20 minutes. The reaction mixture is stirred at −15 to −10° for 1.5 hours and then poured into 2 liters of ice cold saturated sodium bicarbonate solution. More solid sodium bicarbonate is added, as necessary, in order to make the solution weakly basic. After storing the mixture in the refrigeration overnight the resulting crystals are filtered, washed with water and dried to yield 98.2 g (86%) of D,L-4-acetamido-N-acetyl-3-nitrophenylalanine methyl ester, m.p. 123°–125°.

C. D,L-N-Acetyl-4-amino-3-nitrophenylalanine methyl ester

A mixture of 86 g (0.266 mole) of D,L-4-acetamido-N-acetyl-3-nitrophenylalanine methyl ester and 33.7 g (0.318 mole) of sodium carbonate in 2 liters of methanol is heated to reflux for 2 hours. The mixture is filtered hot to remove precipitated salts and the filtrate evaporated to leave an oil. To this oil is added 300 ml of water and upon trituration a crystalline solid is obtained which is filtered and dried to yield 36.3 g (49%) of D,L-N-acetyl-4-amino3-nitrophenylalanine methyl ester, m.p. 133°–134°.

D. D,L-3-(Quinoxalin-6-yl)alanine dihydrochloride

Proceeding as in steps A and B of Example 38 but starting with D,L-N-acetyl-4-amino-3-nitrophenylalanine methyl ester (10 g, 35.6 mmoles) there is obtained 4.52 g (44%), of D,L-3-(quinoxalin-6-yl)alanine dihydrochloride, m.p. 185°–200° (dec.).

EXAMPLE 42

D,L-3-(2,3-Dihydroxyquinoxalin-6-yl)alanine hydrochloride

Proceeding as in step A of Example 27, and steps A and B of Example 40 but starting with 5 gm (17.8 mmoles) of D,L-N-acetyl-4-amino-3-nitrophenylalanine methyl ester (prepared as in step C of Example 41) there is obtained 2.6 g (51%) of D,L-3-(2,3-dihydroxyquinoxalin-6yl)alanine hydrochloride, m.p. 270°–280° (dec.).

EXAMPLE 43

D,L-3-(1,4-Benzoxazin-3-one-7-yl)-2-methylalanine hemihydrochloride

A mixture of D,L-3-carboxymethoxy-4-nitro-α-methyl phenylalanine hydrochloride (8.1 g 28.2 mmoles), prepared as in Example 8, dissolved in 20 ml concentrated hydrochloric acid, and stannous chloride dihydrate (40 g, 177 mmoles) also dissolved in 70 ml concentratd hydrochloric acid is heated on a steam bath for two hours. The mixture is poured into 500 ml water and hydrogen sulfide gas is bubbled through the solution to remove tin salts. The precipitate is filtered off and the filtrate is taken to a small volume. D,L-3-(1,4-benzoxazin-3-one-7yl)-2-methylalanine hemihydrochloride crystallizes out and is filtered to yield 1.1 g (17%) m.p. 308° (dec.).

EXAMPLE 44

D,L-3-(1,4-Benzoxazin-3-one -7-yl)alanine hemihydrochloride

A. D,L-N-acetyl-3-hydroxy-4-nitro-α-cyanophenyl alanine ethyl ester

A solution is formed by adding successively at 0° C. 3-hydroxy-4-nitro benzyl chloride [S.B. Hanna, et al., J. Chem. Soc., 221 (1961)] (18.75 g; 100 mmoles) and potassium t-butoxide (11.3 g; 100 mmoles to 100 ml of dimethyl formamide. In a separate flask, a mixture of ethyl acetamino cyanoacetate (18.75; 110 mmoles) and potassium t-butoxide 12.42 g; 110 mmoles) in 100 ml dimethyl formamide is stirred until a solution is obtained. This solution is then added to the previous solution and the resulting mixture is kept at about 50° C. for several hours. It is then left at room temperature overnight.

Water (250 ml.) is added and the mixture is filtered removing a small amount of organic polymeric material. The filtrate is extracted with ethyl acetate; the organic layer is washed with water. The aqueous layer is then acidified with 5% hydrochloric acid and extracted with ethyl acetate. After drying and evaporation of the ethyl acetate an oil is obtained that crystallizes to yield 22.8 g (71%) of D,L-N-acetyl-3-hydroxy-4-nitro-α-cyano phenylalanine ethyl ester, m.p. 154°–156°.

B.
D,L-N-Acetyl-3-(carboethyoxymethoxy)-4-nitro-α-cyanophenylalanine ethyl ester To D,L-N-acetyl-3-hydroxy-4-nitro-α-cyanophenylalanine ethyl ester (11 g, 34.2 mmoles) in 150 ml acetone is added ethyl bromoacetate (5.8 g, 34.5 mmoles), sodium iodide (5.1 g, 34.2 mmoles) and potassium carbonate (5.1 g, 36.8 mmoles). Reflux is maintained for 24 hours. Half of the volume of acetone is evaporated off and the residue is poured onto water (500 ml). It is extracted with ether, the ether layer is washed with water, and dried over magnesium sulfate. Concentration under vacuum leaves an oil that is crystallized from a mixture of petroleum ether-chloroform (9:1 v/v) yielding 9.1 g (65%), D,L-N-acetyl-3-(carboethoxymethoxy)-4-nitro-α-cyanophenylalanine ethyl ester, m.p. 130°–133°.

C. D,L-3-(1,4-Benzoaxzin-3-one-7-yl)alanine hemihydrochloride

D,L-N-acetyl-3-carboethoxymethoxy-4-nitro-α-cyanophenylalanine ethyl ester (8.6 g, 21.1 mmoles) in concentrated hydrochloric acid (100 ml) is refluxed for five hours after which the solution is evaporated to dryness. The residue is then dissolved in 50 ml concentrated hydrochloric acid, and stannous chloride dihydrate (28.5 g, 126 mmoles) in 50 ml concentrated hydrochloric acid is added. The resulting solution, after being stirred at room temperature for 1 hour, is diluted to about 400 ml with water. Hydrogen sulfide gas is bubbled into the solution. The insoluble tin sulfides are filtered, and the solution is evaporated to dryness. The residue is taken up in 30 ml of 2% hydrochloric acid and crystallization gives 1.42 g (26%) of D,L-3-(1,4-benzoxazin-3-one-7-yl)alanine hemihydrochloride, m.p. 285° (dec.).

EXAMPLE 45

D,L-3-(5-Hydroxy-4H-pyran-4-on-2-yl)-2-methylalanine

To a solution of 1.60 g (0.07 mole) of sodium in 210 ml of ethanol is added 17.73 g (0.07 mole) of iodokojic acid [T. Yabuta, J. Chem. Soc., 575 (1924) and 3 g (0.024 mole) ethyl 2-isocyanopropionate. To the above solution, stirred under a nitrogen atmosphere, is added a solution made up of 1.60 g (0.07 mole) of sodium and 8.9 g (0.07 mole) of ethyl 2-isocyanopropionate in 175 ml of ethanol over a priod of 45 minutes. The reaction is stirred for a further 3 hours at room temperature, evaporated to dryness, the residue dissolved in water and extracted with ethyl acetate. The aqueous phase is acidified with hydrochloric acid and again extracted with ethyl acetate. The ethyl acetate is evaporated and the brick red residue is refluxed in 200 ml of 3 N hydrochloric acid for 15 hours, cooled and extracted with ethyl acetate, treated with charcoal and evaporated to dryness. The residue is redissolved in water, made basic with ammonium hydroxide and evaporated to dryness. Upon addition of 25 ml of water, the product is obtained as a light yellow solid which is filtered and dried. Yield 2.26 g (15%) m.p. 239°–241°.

EXAMPLE 46

D,L-3-(2-Hydroxy-4-pyridyl)-2-methylalanine

A solution of 20 g of crude 4-bromomethyl-2-fluoropyridine [P. T. Sullivan, et al., J. Med. Chem., 14, 211 (1971)], which contains approximately 13 g (73 mmoles) of pure material in 100 ml of dimethylformamide is cooled in an ice bath. To this solution is added a cold solution of 11.3 g (100 mmoles) of methyl 2-isocyanopropionate and 11.2 g (100 mmoles) of potassium t-butoxide in 75 ml of dimethyl formamide. The temperature is allowed to rise to 25° and the reaction is stirred for one hour at 25° after which it is poured into one liter of ice water. The aqueous mixture is extracted with 3 × 200 ml of ether which is backwashed with 2 × 100 ml of water. The ether extracts are dried and evaporated to leave 24 g of a thick oil. To this oil is added with cooling and stirring 100 ml of concentrated hydrochloric acid. The mixture is then refluxed for 1 hour, evaporated to dryness and 100 ml of water again evaporated from the residue. The residue is finally dissolved in 200 ml of water and extracted with 2 × 100 ml of ethyl acetate. From the organic extract there is recovered 4.1 g of 4-dibromomethyl-2-hydroxypyridine, m.p. 159°–160°, resulting from the hydrolysis of 4-dibromomethyl-2-fluoropyridine present as an impurity in the starting material.

The aqueous fraction is warmed to 80° with 1 g of charcoal for 30 minutes, filtered, evaporated and the residue taken up in 50 ml of water, basified with concentrated ammonium hydroxide, and evaporated. The residue is treated with 10 ml of water, cooled and filtered to give 2.2 g (11.2 mmoles, 15.5%) of D,L-3-(2-hydroxy-4-pyridyl)-2-methylalanine, m.p. 315°–316° (dec.).

EXAMPLE 47

D,L-3-Cyano-α-methyltyrosine methyl ester hydrochloride

A. 3-(Diacetoxymethyl)-4-acetoxybenzyl chloride

3-Formyl-4-hydroxy benzyl chloride (675 g., 3.96 moles) in 3.5 liters of acetic anhydride is refluxed for 24 hours. The reaction mixture is evaporated to dryness, triturated with a minimum amount of ether and filtered to yield 987 g. (79%) of 3-(diacetoxymethyl)-4-acetoxybenzyl chloride, m.p. 93°–95°.

B. 3-(Diacetoxymethyl)-4-acetoxybenzyl iodide 3-(Diacetoxymethyl)-4-acetoxybenzyl chloride (987 g., 3.14 mole) and sodium iodide (494 g., 3.29 moles) in 3.5 liters acetone are refluxed for 6 hours. The reaction mixture is filtered, the filtrate is evaporated to dryness, triturated in ether and filtered to yield 1,162 g (91%) of 3-(diacetoxymethyl)-4-acetoxybenzyl iodide, m.p. 117°–120° C.

C. D,L-3-Formyl-α-methyltyrosine methyl ester hydrochloride hydrate

The anion of methyl 2-isocyano propionate is prepared by adding at −50° C. methyl 2-isocyanopropionate (167 ml., 1.5 moles) to a solution of potassium t-butoxide (165 g., 1.5 moles) in 700 ml dimethyl formamide. To a solution of 3-(diacetoxymethyl)-4-acetoxybenzyl iodide (500 g., 1.23 moles) in 1.5 liter DMF cooled to −10° C. is added the freshly prepared anion solution over a period of 20 minutes. Towards the end of this reaction, the temperature is about 5° and the mixture is stirred at room temperature for 2 hours. It is then poured into cold water, extracted with ethyl acetate, washed with water, dried and evaporated to dryness to yield methyl D,L-2-methyl-2-isocyano-3-[3-diacetoxymethyl)-4-acetoxyphenyl]-2-propionate (430 g., 89%). This intermediate is dissolved in 2.2 liters of ethyl acetate and 10 ml concentrated hydrochloride acid in 30 ml water is added slowly. External cooling is necessary to maintain the temperature at about 20°-25°. The mixture is then neutralized with sodium bicarbonate, washed with water dried and evaporated to dryness to yield D,L-N-formyl-α-methyl-3-diacetoxymethyl-4-acetoxyphenylalanine methyl ester (410 g., 91%). This derivative is dissolved in 2 liters of methanol, 150 ml concentrated hydrochloric acid is added and the resulting mixture is stirred at room temperature for 3 days. The solution is evaporated to dryness, triturated in ether and filtered. The solid is then treated with a minimum amount of hot isopropanol. It is then cooled and filtered, washed with ether and air-dried to yield D,L-3-formyl-α-methyltyrosine methyl ester hydrochloride monohydrate (151 g, 42% from 3-(diacetoxy-methyl)-4-acetoxybenzyl iodide), m.p. 145°-150° C. (dec.).

D. D,L-3-Cyano-N-formyl-α-methyltyrosine methyl ester

Refluxing D,L-3-formyl-α-methyltyrosine methyl ester hydrochloride hydrate (119 g, 0.41 moles) with hydroxylamine hydrochloride (54 g, 0.78 moles) and sodium formate (95 g, 1.4 moles) in 1.2 liters of formic acid for three hours affords 72 g (67%) of D,L-3-cyano-N-formyl-α-methyltyrosine methyl ester.

E. D,L-3-Cyano-α-methyltyrosine methyl ester hydrochloride

A mixture of 40 ml of concentrated HCl and 3.68 g (15 mM) of D,L-3-cyano-N-formyl-α-methyltyrosine methyl ester is refluxed for 1 hour. After cooling, to room temperature, the crystals are filtered and washed with diethyl ether to yield about 2.06 grams (54%) of D,L-3-cyano-α-methyltyrosine methyl ester hydrochloride, m.p. 267° (dec.).

EXAMPLE 48

L-α-Methyl-4-(pyrrol-1-yl)phenylalanine

A. L-α-Methylphenylalanine methyl ester hydrochloride methanol

To 210 ml of methanol is added 47 ml of thionyl chloride over a 30 minute period. To this solution is added 98 g (0.50 mol) of L-α-methylphenylalanine hydrate (F. W. Bollinger, J. Med. Chem., 14, 373 (1971) with cooling. The reaction is then stirred and heated at 50° for 16 hours, after which the mixture is evaporated to dryness. The residue is slurried with 500 ml of ether and the resulting solid filtered to yield 124 g. (approximately 100%) of L-α-methylphenylalanine methyl ester hydrochloride methanolate, m.p. 103°-104°.

B. L-N-Formyl-α-methylphenylalanine methyl ester

To a suspension of 124 g. (0.50 mole) of L-α-methylphenylalanine methyl ester hydrochloride methanolate in 65 ml of formic acid is added 41 g. (0.60 mole) of sodium formate with stirring and cooling in an ice bath. After 15 minutes, 82 ml. of formic acetic anhydride is added to the stirred and cooled mixture at 25° for 18 hours, after which a further 82 ml of formic acetic anhydride is added and the reaction left for a further 3 hours after which time it is complete. The insoluble salts are removed by filtration and washed with 100 ml each of ether and chloroform. The washings are combined with the filtrate and the whole evaporated to give a thick oil which is stirred with cold water (500 ml.) for 1.5 hours. This mixture is then extracted with 3 × 500 ml of chloroform and the combined chloroform extracts washed with 200 ml of 1N hydrochloric acid, 200 ml water, 5% sodium bicarbonate until the aqueous wash remained basic and finally with 2 × 100 ml of water. After drying of the chloroform solution, evaporation and trituration of the residue with petroleum ether there is obtained a crystalline solid, which is recovered by filtration to give 98.4 g (89%) of L-N-formyl-α-methylphenylalanine methyl ester, m.p. 55°-58°.

C. L-N-Formyl-α-methyl-4-nitrophenylalanine methyl ester

To 250 ml of 90% nitric acid maintained between −15° and −10° is added in portions over 0.5 hour 97.8 g (0.44 moles) of L-N-formyl-α-methylphenylalanine methyl ester. The reaction is maintained at this temperature for 1 hour longer then poured slowly in 2000 ml of an ice-water slush containing 200 g of sodium bicarbonate. More sodium bicarbonate is added, if necessary, in order to bring the pH up to 7. The gummy product which precipitates becomes a granular solid when the mixture is stirred mechanically for 1 hour, and after recovering by filtration, washing with 500 ml. of water and drying, there is obtained 99.4 g. (84%) of L-N-formyl-α-methyl-4-nitrophenylalanine methyl ester, m.p. 90°-95°.

D. L-4-Amino-N-formyl(α-methylphenylalanine methyl ester

Starting with 98.9 g. (0.35 mole) of L-N-formyl-α-methyl-4-nitrophenylalanine and following the procedure of part C of Example 11, but omitting the final recrystallization, there is obtained 69.3 g (83.5%) of L-4-amino-N-formyl-α-methylphenylalanine methyl ester, m.p. 70°-76°.

E. L-N-Formyl-α-methyl-4-(pyrrol-1-yl)phenylalanine

A mixture of 10 gm (42 mmoles) of L-4-amino-N-formyl-α-methylphenylalanine methyl ester, 5.6 g (42 moles) of 2,5-dimethoxytetrahydrofuran, 50 g of Amberlite$^R$ IRC 50(H) resin and 250 ml of toluene is heated and stirred at reflux for 4 hours. Filtration to remove the resin and evaporation of the filtrate leaves a semisolid residue of 8.9 g, which after slurrying with 25 ml of ether and recovering the insoluble product by filtration yields 6.15 g (51%) of L-N-formyl-α-methyl-4-(pyrrol-1-yl)phenylalanine methyl ester, m.p. 106°-109°.

F. L-α-Methyl-4(pyrrol-1-yl)phenylalanine

A mixture of 12 g (42 mmoles) of L-N-formyl-α-methyl-4-(pyrrol-1-yl)phenylalanine methyl ester,, 48 ml of 40% aqueous sodium hydroxide and 180 ml of methanol is heated to reflux for 5 hours after which it is evaporated to dryness. The residue is dissolved in 300 ml. of water and sufficient 12N hydrochloric acid is added to bring the pH to about 5, whereupon the product crystallizes. It is recovered by filtration, washed with 50 ml each of water, ethanol and ether and finally dried in vacuum at 50° for 18 hours to yield 8.3 g (81%) of L-α-methyl-4-(pyrrol-1-yl)phenylalanine, m.p. 294°–295° (dec.).

EXAMPLE 49

D-α-Methyl-4-(pyrrol-1-yl)phenylalanine

Starting with 18.7 gm (95 mmoles) of D-α-methylphenylalanine hydrate (F. W. Bollinger, J. Med. Chem. 14, 373 (1971) and following the procedures of parts A, B C, D, E and F of Example 48 for the synthesis of the L-isomer, there is obtained 3.7 gm. (15.8% overall yield) of D-α-methyl-4-(pyrrol-1-yl)phenylalanine, m.p. 297°–299°.

EXAMPLE 50

L-α-Methyl-4-(pyrrol-1-yl)phenylalanine methyl ester hydrochloride

To a stirred suspension of 3 g (12.3 mmoles) of L-α-methyl-4-(pyrrol-1-yl)phenylalanine (prepared as in Example 48) in 200 ml of methanol is added dropwise, and with stirring, at 25° an etheral solution of diazomethane until the yellow color of diazomethane is no longer dissipated, at which point a homogenous solution is obtained. The reaction mixture is then evaporated to leave 3 g of an oil. Two grams of this oil are dissolved 45 ml of warm hexane and upon cooling, there is obtained 1.2 g of the methyl ester as the free base, m.p. 40°–41°. This material is dissolved in 100 ml D,L- and an excess of hydrogen chloride gas is -methylphenylalanine the solution to precipitate 1.3 g (54%) of L-α-methyl-4-(pyrrol-1-yl)phenylalanine methyl ester hydrochloride, m.p. 200°–202°.

EXAMPLE 51

D,L-4-[2-(Carboxy)pyrrol-1-yl]-2-methylphenylalanine dihydrate

A.

D,L-4-[2-(Carbomethoxy)pyrrol-1-yl]-N-formyl-α-methylphenylalanine methyl ester

A mixture of 5.0g (21 mmoles) of D,L-4-amino-N-formyl-α-methylphenylalnine methyl ester (prepared as in Part C of Example 11) and 4.03 g (21 mmoles) of 2-carbomethoxy-2,5-dimethoxytetrahydrofuran in 40 ml of acetic acid is heated on the steam bath for 1.5 hours, cooled and poured into 300 ml of cold water. The aqueous mixture is extracted with 3 × 100 ml of ethyl acetate and the combined organic extracts washed with 0.5N sodium hydroxide until the aqueous washings remain basic, and finally with water. After drying and evoprating the organic layer, the residual oil is chromatographed or silica gel to give 4.0 g of D,L-4-[2-(carbomethoxy)pyrrol-1-yl]-N-formyl-α-methylphenylalanine methyl ester as an oil which is satisfactory for use in the next reaction.

B.

D,L-4-[2-(Carboxy)pyrrol-1-yl]-α-methylphenylalanine dihydrate

A mixture of 3.6g (10.5mmoles) of D,L-4-]2-(carbomethoxy) pyrrol-1-yl]-N-formyl-α-methylphenylalanine methyl ester and 12 ml of 40% aqueous sodium hydroxide in 45 ml of methanol is heated to reflux for 2.5 hours, cooled and evaporated to dryness. The residue is redissolved in 30 ml of water and the solution made slightly acidic by addition of acetic acid. The resulting crystalline precipitate is recovered by filtration, washed with 20 ml of water, 20 ml of methanol and 100 ml of ether and dried in vacuum at 50° to give 1.64 g. (48%) of D,L-4-[2-(carboxy)pyrrol-1-yl]-α-methylphenylalanine dihydrate, m.p. 304°–306° (dec.).

EXAMPLE 52

D,L-α-Methyl-3-(pyrrol-1-yl)phenylalanine hydrochloride

A. D,L-N-Formyl-α-methyl-3-nitrophenylalanine methyl ester

Methyl 2-isocyanopropionate (7.95 g, 70.2 mmoles) is added slowly to a suspension of sodium methoxide (20% excess) in 40 ml. of dry dimethylformamide at −5°. The resultant solution is added slowly to a solution of 3-nitrobenzylchloride (10 g, 58.5 mmoles) in 40 ml of dimethylformamide at −5°. After the addition is complete the reaction mixture is allowed to reach room temperature. The mixture is added with stirring to a mixture of ice and water and extracted with ethyl acetate. The ethyl acetate extracts are combined and stirred with a few ml of concentrated hydrochloric acid for 2 hours at room temperature. The ethyl acetate solution is rinsed with water, 5% sodium bicarbonate, water and dried. The solution is filtered and evaporated to yield 13.50 g (87%) of D,L-N-formyl-3-nitrophenylalanine methyl ester, m.p. 120°–122°.

B. D,L-3-Amino-N-formyl-α-methylphenylalanine methyl ester

D,L-N-formyl-α-methyl-3-nitrophenylalanine methyl ester (43.09 g, 0.162 moles) suspended in 200 ml methanol is hydrogenated on a Parr hydrogenator using 2 g of 5% palladium on charcoal. The catalyst is filtered off and the filtrate is evaporated to dryness to yield 37.8 g (98%) of D,L-3-amino-N-formyl-α-methylphenylalanine methyl ester as an oil which is sufficiently pure for use in the next step.

C. D,L-α-methyl-3-(pyrrol-1-yl)phenylalanine hydrochloride

To D,L-3-amino-N-formyl-α-methylphenylalanine methyl ester (35.1g, 148.5 mmoles) dissolved in 180 ml glacial acetic acid is added 2,5-dimethoxytetrahydrofuran (21.5 g, 163 mmoles). The mixture is heated on a steam bath for 30 minutes. It is then poured onto ice and water (2 liters) and extracted 5 times with 200 ml of chloroform. The extracted are combined, washed twice with 5% aqueous sodium bicarbonate, once with water and dried with magnesium sulfate. Evaporation to dryness leaves 38.5 g of brown oil which is then absorbed on 500 g of silica gel and eluted with chloroform to yield 19.9 g (44%) of D,L-α-methyl-3-(pyrrol-1-yl)phenylalanine methyl ester, m.p. 80°–83°.

The ester (6 g, 21 mmole) is dissolved in 80 ml methanol 15 ml 40% sodium hydroxide is added and the resulting mixture is refluxed for 16 hours. The reaction mixture is evaporated to dryness. The residue is dissolved in water and glacial acetic acid is added to adjust the pH to 6. The fine light cream precipitate is filtered, rinsed with water and air dried. This solid is added to 30 ml of 6N hydrochloric acid, the suspension is stirred at room temperature for 90 minutes. It is then filtered, washed with isopropanol, with ester and then air dried to yield 5.15 g of D,L-α-methyl-3-(pyrrol-1-yl)phenylalanine hydrochloride, m.p. 205°–207° (dec.).

EXAMPLE 53

D,L-4-(Pyrrol-1-yl)phenylalanine

A. D,L-4-Amino-N-formylphenylalanine methyl ester

Using 1.0 g of 5% palladium on charcoal as catalyst, 52.7 g (0.21 moles) of D,L,N-formyl-4-nitrophenylalanine methyl ester (prepared as in part A of Example 30) in 200 ml of methanol is reduced under 18.1 kg of hydrogen pressure. The catalyst is filtered off and the filtrate evaporated to yield 44 gm (94%) of D,L-4-amino-N-formylphenylalanine methyl as oil suitable for use in the next reaction.

G. N-Formyl-4-(pyrrol-1-yl) phenylalanine

Under a stream of nitrogen, 44 grams (0.2 moles) D,L-d,L-4-amino-N-formylphenylalanine methyl ester and 30.5 g (0.23 mole) of 2,5-dimethoxytetrahydrofuran dissolved in 250 ml of acetic acid is heated on a steam bath for 0.5 hour. The reaction mixture is dilute with 600 ml of $H_2O$ and extracted with chloroform. Some NaCl is added to break up the emulsion. The chloroform layer is washed with $H_2O$ and dilute bicarbonate solution, dried over $MgSO_4$ and evaporated. The residual oil is purified by chromatography over silica gel to yield 31.5 g (57.5%) of D,L-N-formyl-4-(pyrrol-1-yl)phenylalanine methyl ester, m.p. 117°–118°.

C. D,L-4-(pyrrol-1-yl)phenylalanine

Under a gentle stream of nitrogen, a mixture of 5.4 g (20 mmole) of D,L-N-formyl-4-(pyrrol-1-yl)phenylalanine methyl ester, 16 ml of 7N NaOH and 75 ml of methanol is refluxed for 3 hours. The methanol is evaporated off and the residue take up in $H_2O$. Dilute HCl is added to obtain an acidic mixture. Dilute $NH_4OH$ is then added to obtain a basic mixture. The solid is filtered and washed with $H_2O$. The solid is recrystallized from 700 ml of 2N $NH_4OH$ to yield 2.6 g (50%) of D,L-4-(pyrrol-1-yl)phenylalanine, m.p. 288° (dec.).

EXAMPLE 54

D,L-α-Methyl-4-(pyrrol-1-yl)phenylalanine methyl ester

Diazomethane (34 mmole) in diethyl ether (Fieser & Fieser; Reagents for Org. Syn. p 192) is added in portions to a suspension of 2.0 g (8.2 mole) of D,L-α-methyl-4-(pyrrol-1-yl)phenylalanine from part E of Example 11 in 50 ml of methanol at 0°. A solution is obtained after 1 hour of stirring at room temperature. Dilute acetic acid in diethyl ester is then added dropwise until the yellow color fades. The solution is filtered and evaporated. The residual solid is recrystallized from n-hexane., m.p. 93°–94°.

D,L-α-Methyl-3-[4-(pyrrol-1-yl)phenyl]alanine methyl ester (1.0 g ) is dissolved in 25 ml of diethyl ether. Dry HCl gas is bubbled into the solution. The crystalline product is filtered and dried at 100° to yield 1.1 g (97%) of D,L-α-methyl-4-(pyrrol-1-yl) phenylalanine methyl ester hydrochloride, m.p. 207° (dec.)

EXAMPLE 55

D,l-3-Hydroxy-α-methyl-4-(pyrrol-1-yl) phenylalanine hydrate

A. D,L-N-Formyl-3-hydroxy-α-methyl-4-(pyrrol-1-yl) phenylalanine methyl ester Using 2 g. of 10% palladium on carbon as catalyst, 25 g (88 mmole) of D,L-N-formyl-3-hydroxy-α-methyl-4-nitrophenylalanine methyl ester from part A of Example 6 dissolved in 300 ml of methanol is reduced using a Parr hydrogenator. The catalyst is filtered off and the filtrate evaporated to obtain 21.1 g (95%) of an oil which is of sufficient qualtity for the next step.

To a solution of 16.3 g (65 mmole) of D,L-4-amino-N-formyl-3-hydroxy-α-methylphenylalanine methyl ester, as prepared above, in 100 ml of acetic acid is added in one portion 9 g (68 mmole) of 2,5-dimethoxytetrahydrofuran. The solution is refluxed for 30 minutes and then poured into ice and water. The aqueous mixture is extracted with ethyl acetate. The organic layer is washed with dilute sodium bicarbonate and water, dried over $Na_2SO_4$, filtered and evaporated. The residue is purified on silica gel to yield 6.12 g (30%) of D,L-N-formyl-3-hydroxy-α-methyl-4-(pyrrol-1-yl)phenylalanine methyl ester, m.p. 132°–135°.

B. D,L-3-Hydroxy-α-methyl-4-(pyrrol-1-yl)phenylalanine hydrate

In a glass bomb is placed 20 ml of 40% NaOH, 50 ml of methanol and 5 g (16 mmole) of D,L-N-formyl-3-hydroxy-α-methyl-4-(pyrrol-1-yl) phenylalanine methyl ester. The sealed bomb is heated at 120° for 1 hour. The cooled solution is evaporated and the residue redissolved in 50 ml of water. The solution in neutralized with acetic acid and the product is filtered, washed with water and dried in a vacuum oven at 50° for 18 hours to yield 4.0 g (87%) of D,L-3-hydroxy-α-methyl-4-(pyrrol-1yl)-phenylalanine hydrate, m.p. 315° (dec.)

EXAMPLE 56

D,L-3-Methoxy-α-methyl-4-(pyrrol-1-yl)phenylalanine oxalic acid salt

With magnetic stirring, a mixture of 3.5 g (26 mmole) of methyliodide, 2 g (14 mmole) of potassium carbonate, 120 ml of acetone and 4.0 g (13 mmole) of D,L-N-formyl-3-hydroxy-α-methyl-4-(pyrrol-1-yl)phenylalanine methyl ester (from part A of Example 55) is refluxed for 5 hours. The mixture is filtered and the filtrate evaporated. The residue is dissolved in ethyl acetate, washed with water, dried over $Na_2SO_4$, filtered and evaporated to obtain 4.3 g (93%) of an oil which is of sufficient purity for the next step.

A solution of 12 ml of 40% NaOH, 40 ml of methanol and 4.3 g 813 mmole) of D,L-N-formyl-3-methoxy-α-methyl-4-(pyrrol-1-yl)phenylalanine methyl ester prepared as above is refluxed for 3 hours with magnetic stirring. The solution is evaporated and the residue redissolved in 40 ml of water. The solution is neutralized with hydrochloric acid and the product is filtered, washed with water and dried in a vacuum oven at 50° for 18 hours to yield 3.27 g (92%) m.p. 230° (dec.).

The oxalic acid salt is prepared by magnetically stirring for 1 hour, a mixture of 1.0 (11 mmole) of oxalic acid, 50 ml of methanol and 3.0 g (11 mmole) of D,L-3-methoxy-α-methyl-4-(pyrrol-1-yl)phenylalanine prepared above. Insoluble impurities are filtered off and the filtrate treated with charcoal. The solution is evaporated and the residue washed with diethyl ether to remove excess oxalic acid to yield 3.15 g (78%) of D,L-3-methoxy-α-methyl-4-(pyrrol-1-yl)phenylalanine oxalate, m.p. 188° (dec.)

EXAMPLE 57

D,L-α-Methyl-3-(pyrrol-1-yl)tyrosine oxalate monohydrate

A. D,L-α-Methyl-3-nitrotyrosine methyl ester hydrochloride

A solution of 42.0 g (180 mmole) of D,L-α-methyl-3-nitrotyrosine [prepared as described by Saari, et al., J. Med Chem., 10, 1008 (1967)] in 200 ml of methanol saturated with dry hydrogen chloride is heated to reflux for 10 hours, evaporated to dryness and the residue slurried with 200 ml of ether. The solid is recovered by filtration to give 50 g (97%) of D,L-α-methyl-3-nitrotyrosine methyl ester hydrochloride, m.p., 202°–203° (dec.).

B. D,L-N-Formyl-α-methyl-3-nitrotyrosine methyl ester

To a solution of 50 g of D,L-α-methyl-3-nitrotyrosine methyl ester hydrochloride in 200 ml of formic acid is added 100 ml of formic acetic anhydride, and the mixture stirred at 25° for 2 hours. A precipitate is filtered off and the resulting solid (9.5 g) identified as D,L-N-formyl-α-methyl-3-nitrotyrosine. The filtrate is evaporated to dryness and the residue slurried with 100 ml of water and filtered to give 37 g of crude product. This is suspended in 200 ml of water and the mixture extracted with 3 × 200 ml of ethyl acetate. From the ethyl acetate extracts there is obtained, after drying and evaporation, 30.8 g (78%) of D,L-N-formyl-α-methyl-3-nitrotyrosine methyl ester, m.p. 129°–132°.

C. D,L-3-Amino-N-formyl-α-methyltyrosine methyl ester

To a solution of 20 g (71 mmole) of D.L-N-formyl-α-methyl-3-nitrotyrosine methyl ester in 300 ml of methanol is added 2.0 g of 10% palladium on charcoal and the resulting mixture reduced under 18.1 kg of hydrogen pressure for 30 minutes. The reaction mixture is filtered and the filtrate evaporated to dryness. The crystalline residue is slurried with 25 ml of methanol and the solid recovered by filtration to yield 15.5 g (86%) of D,L-3-amino-N-formyl-α-methyltyrosine methyl ester, m.p. 197°–199°.

D. D,L-N-Formyl-α-methyl-3-(pyrrol-1-yl)tyrosine methyl ester

A solution of 15 g (60 mmole) of D,L-3-amino-N-formyl-α-methyltyrosine methyl ester and 6.2 ml (66 mmole) of 2,5-dimethoxytetrahydrofuran in 80 ml of acetic acid is heated to reflux for 30 minutes. The reaction mixture is then poured into 400 ml of ice and water which is then extracted with 3 × 200 ml of ethyl acetate. The combined ethyl acetate extracts are washed with 1N sodium bicarbonate until the aqueous layer remains basic, dried and concentrated. The residue is purified by passage through a column of silica gel. Elution with ethyl acetate gives 7.3 g (40%) of crystalline D,L-N-formyl-α-methyl-3-(pyrrol-1-yl)tyrosine methyl ester, m.p. 151°–152°.

E. D,L-α-Methyl-3-(pyrrol-1-yl)tyrosine oxalate monohydrate

A mixture of 2.0 g (6.6 mmole) of D.L-N-formyl-α-methyl-3-(pyrrol-1-yl)tyrosine methyl ester, 8 ml of 40% aqueous sodium hydroxide and 30 ml of methanol is heated to reflux for 4 hours. The solvent is evaporated and the residue dissolved in 50 ml of water, made acidic with concentrated hydrochloric acid and then made weakly basic (pH 9) with ammonium hydroxide. The solution is then evaporated to dryness and the residue is stirred with 50 ml of water for 30 minutes and the insoluble material recovered by filtration to give 1.51 g of crude product. The crude material is added to 25 ml of methanol, followed by addition of 540 mg of oxalic acid. Insoluble impurities are removed by filtration and the filtrate is evaporated to dryness. From the residue, 50 ml of water is evaporated and the residue dried under vacuum at 50° for 5 hours to give 1.66 g (68%) of D,L-α-methyl-3-(pyrrol-1-yl)tyrosine oxalate monohydrate, m.p. 105°–115°.

EXAMPLE 58

D,L-4-Methoxy-α-methyl-3-(pyrrol-1-yl)phenylalanine oxalate monohydrate

A. D,L-N-Formyl-4-methoxy-α-methyl-3-(pyrrol-1-yl)phenylalanine methyl ester

A mixture of 3.5 g (11.6 mmole) of D,L-N-formyl-α-methyl-3-(pyrrol-1-yl)tyrosine methyl ester (prepared as in part D of Example 57) 1.7 g of potassium carbonate and 3.0 g of methyl iodide in 120 ml of acetone is heated to reflux for 8 hours. The acetone is removed by evaporation and the residue dissolved in 150 ml of ethyl acetate. The ethyl acetate solution is washed with 2 × 100 ml of water, dried and evaporated to yield 3.6 g of D,L-N-formyl-4-methoxy-α-methyl-3-(pyrrol-1-yl)phenylalanine methyl ester as an oil which is suitable for use in the next reaction.

B. D,L-4-Methoxy-α-methyl-3-(pyrrol-1-yl)phenylalanine oxalate monohydrate

The hydrolysis of 3.6 g (11.3 mmole) of D.L-N-formyl-4-methoxy-α-methyl-3-(pyrrol-1-yl)phenylalanine methyl ester is carried out according to the procedure in Example 56 to give 1.9 g of crude amino acid. This material is converted to the oxalate by the procedure of Example 56 to yield 1.83 g (42%) of D,L-4-methoxy-α-methyl-3-(pyrrol-1-yl)phenylalanine oxalate monohydrate, m.p. 100°–110°.

EXAMPLE 59

D,L-4-(Indol-1-yl)-α-methylphenylalanine hydrate

A. p-(Indol-1-yl)benzoic acid

A mixture of 180 ml of 6N NaOH, 360 ml ethylene glycol and 39.3 g (180 mmole) of 1-p-cyanophenylindole (Misbahul Ain Khan and J. B. Polya, J. Chem. Soc., 85 (1970)] is refluxed for 3 hours at 150°. The basic solution is diluted with 450 ml of H$_2$O and extracted with diethyl ether to remove neutrals. The aqueous solution is acidified with 200 ml of 6N HCl. The solid is filtered washed with hot water and dried in a vacuum oven at 50° to yield 45.8 g (95%) of p-(indol-1-yl)benzoic acid, m.p. 224°–226°.

B. 1-(p-Hydroxymethyl)phenylindole

To a mechanically stirred suspension of 12.5 g (330 mmole) of LiAlH$_4$ in 600 ml of diethyl ether is added dropwise 45.8 g (180 mmole) of p-(indol-1-yl)benzoic acid dissolved in 458 ml of dry tetrahydrofuran. The reaction mixture is stirred at 0° for 2 hours and then decomposed by sequential addition of 12.5 ml H$_2$O, 12.5 ml of 15% NaOH and 37.5 ml of H₂O. The salts are filtered and washed with diethyl ether. The filtrate is evaporated to dryness, redissolved in diethyl ether and washed with H₂O 1N NaOH solution and H₂O. The ether solution is dried over Na₂SO₄, filtered and evaporated. The oil is dried in a vacuum oven at 50° overnight. The oil crystallizes slowly over several days to yield 27.8 g (68%) of 1-(p-hydroxymethyl)phenylindole, m.p. 37°-39°.

C. D,L-N-Formyl-4-(indol-1-yl)-α-methylphenylalanine methyl ester

To a solution of 11.15 g (50 mmole) of 1-(p-hydroxymethyl)phenylindole in 250 ml of benzene is added in portions 11.9 g (57 mmole) of PCl₅. The mixture is stirred at about 10° for 15 minutes. Insolubles are filtered off and the filtrate washed with 2 × 100 ml of ice water, dried over Na₂SO₄, filtered and evaporated to yield 14 g of an oil which is of sufficient quality for the next step.

A solution of 14 g of p-(indol-1-yl)benzylchloride, prepared as above, dissolved in 75 ml of DMF is stirred magnetically at −45°. To this solution is added over 5-10 minutes, an anion solution prepared by the addition of 8.48 g (75 mmole) of methyl 2-isocyanopropionate to 4.05 g (75 mmole) of sodium methoxide contained in 75 ml of DMF at −45°. The temperature of the resultant mixture is permitted to gradually rise to −15°. Water (900 ml) is then added, not allowing the temperature to exceed 10°. The mixture is extracted with ethyl acetate which is then evaporated. The residue is taken up in diethyl ether, washed with H₂O dried over Na₂SO₄, filtered and evaporated to yield 15.9 g of an oil which is hydrolyzed as such.

32.9 g. of crude methyl 2-isocyano-3-[4-(indol-1-yl)phenyl]2-methylpropionate prepared as above, is dissolved in 300 ml of ethyl acetate at 5° and with magnetic stirring is added dropwise 2.5 ml of concentrated HCl. After stirring for 15 minutes, the solution is diluted with H₂O. The separated organic layer is dried over Na₂SO₄, filtered and evaporated. The crude product is purified on silica gel to yield 25 g. (66% overall). The product is recrystallized from benzene to give D,L-N-formyl-4-(indol-1-yl)phenylalanine methyl ester of m.p. 146°-148°.

D. D,L-4-(Indol-1-yl)-α-methylphenylalanine hydrate

A mixture of 25 ml of 3N NaOH solution, 100 ml of methanol, and 3.0 g (9 mmole) of D,L-N-formyl-4-(indol-1-yl)-α-methylphenylalanine methyl ester is refluxed on a steam bath for 1.5 hours. The methanol is evaporated off and 50 ml of H₂O added. The solution is then refluxed in an oil bath at 115° for 4 hours with a nitrogen atmosphere being maintained throughout hydrolysis. A solution of 27 ml of 3N HCl is added to the cooled solution followed by 10 ml of 1N sodium acetate solution to give a pH of 3.0. The solid is filtered, washed with some hot water and dried overnight in a vacuum oven at 60° to yield 2.59 g (88%) of D,L-4-(indol-1-yl)-α-methylphenylalanine hydrate, m.p. 270°-273°.

EXAMPLE 60

D,L-4-(Carbazol-9-yl)-α-methylphenylalanine

A. 9-(p-Hydroxymethyl)phenylcarbazole

To a mechanically stirred suspension of 4.7 (124 mmole) of LiAlH₄ in 300 ml of diethyl ether is added dropwise 18 g (62 mmole) of 9-(p-carboxy)phenyl carbazole (C.A. Vol. 34, p. 1658) dissolved in 120 ml of dry tetrahydrofuran. The reaction mixture is stirred at 5° for 1 hour and then decomposed by sequential addition of 4.7 ml of H₂O, 4.7 ml of 15% NaOH and 14.1 ml of H₂O. The salts are filtered and washed with diethyl ether. The filtrate is evaporated to dryness, redissolved in diethyl ether, washed with H₂O, dried over Na₂SO₄, filtered and evaporated to yield 15.1 g (88%) of 9-(p-hydroxymethyl) phenyl carbazole. A sample recrystalized from cyclohexane has m.p. 121°-122°.

B. p-(Carbazol-9-yl)benzylchloride

To a suspension of 8.19 (30 mmole) of 9-(p-hydroxymethyl)phenyl carbazole in 150 ml of benzene is added in portions 8.22 g (40 mmole) of PCl₅. The mixture is stirred at about 10° for 15 minutes after which a homogenous solution is obtained. Water (75 ml) is added in portions to the benzene solution. The layers are separated and the organic layer washed with H₂O, dried over Na₂SO₄, filtered and evaporated. The oil is treated with petroleum ether and the resulting solid is filtered and dried to yield 9.5 g (95%) of p-(carbazol-9-yl)benzylchloride, m.p. 88°-89°.

C. Methyl D,L-3-[4-(carbazol-9-yl)phenyl]-2-isocyano-2-methyl propionate

A solution of 9.0 g (30 mmole) of p-carbazol-9-yl)benzylchloride dissolved in 45 ml of DMF is stirred magnetically at −45°. To this solution is added over 5-10 minutes, an anion solution prepared by the addition of 5.8 g (51 mmole) of methyl 2-isocyanopropionate to 2.75 g (51 mmole) of sodium methoxide contained in 75 ml of DMF at −45°. The resultant mixture is permitted to gradually rise to −15°. 700 ml of H₂O is then added and the mixture extracted with ethyl acetate. The ethyl acetate layer is washed with H₂O, dried over Na₂SO₄, filtered and evaporated. The residue is washed with 3 × 55 ml petroleum ether to leave 6.2 g (56%) of methyl D,L-3-[4-(carbazol-9-yl)phenyl]-2-isocyano-2-methyl propionate as an oil which can be used as such in the subsequent reaction. A sample recrystllized from petroleum ether has m.p. 103-105°.

D. D,L-4-(Carbazol-9-yl)-N-formyl-α-methylphenylalanine methyl ester

To a solution of 6.2 g (16.8 mmole) of methyl D,L-3-[4-)carbazol-9-yl)phenyl]-2-isocyano-2-methyl propionate in 100 ml of ethyl acetate, cooled to 5° is added with stirring 1 ml of 12N hydrochloric acid. After stirring for 15 minutes the solution is washed with 2 × 50 ml of water. The oganic layer is dried (Na₂SO₄) and evaporated and the residue crystallized from benzene to yield 5 g (77%) of D,L-4-(carbazol-9-yl)-N-formyl-α-methylphenylalanine methyl ester, m.p. 167°-170°.

E. D,L-4-(Carbazol-9-yl)α-methylphenylalanine

A mixture of 25 ml of 3N NaOH solution, 100 ml of methanol, and 3.0 g (7.7 mmole) of D,L-4-(carbazol-9-yl)-N-formyl-α-methylphenylalanine methyl ester is refluxed on a steam bath for 1.5 hours. The methanol is evaporated off and 50 ml of H₂O added. The solution is then refluxed in an oil bath at 115° for 4 hours with a nitrogen atmosphere being maintained throughout hydrolysis. 27 ml of 3N HCl is added to the cooled solution followed by 10 ml of 1N sodium acetate solution.

The solid is filtered, washed with water and dried overnight in a vacuum oven at 50° to yield 2.55 g(94%) of D,L-4-(carbazol-9-yl)-α-methylphenylalanine, m.p. 271°-274°.

EXAMPLE 61

D,L-3-(Imidazol-2-yl)α-Methyltyrosine Dihydrochloride

A. D,L-N-Formyl-α-Methyl-3-Thiocarbamoyltyrosine Methyl Ester A solution of D,L-3-cyano-N-formyl-α-methyltyrosine methyl ester (1.5 g.; 5.7 mmoles) prepared as described in Part D of Example 47, in 15 ml. pyridine and 2 ml. triethylamine is saturated with hydrogen sulfide and heated at 70° C. in a glass bomb for 18 hours. The reaction mixture is evaporated to dryness, dissolved in ethyl acetate, washed with water, dried and evaporated to dryness. The residue is dissolved in 10 ml. chloroform from which D,L-N-formyl-α-methyl-3-thiocarbamoyltyrosine methyl ester (1.36 g.; 85%) crystallizes out; m.p. 177°-179° (dec.).

B.
D,L-N-Formyl-α-Methyl-3-(Methylthiocarboximidato)-Tyrosine Methyl Ester

D,L-N-Formyl-α-methyl-3-thiocarbamoyltyrosine methyl ester from Part A of Example 61 (14.75 g.; 50 mmoles) is suspended in 150 ml. acetone and 4.35 ml. methyl fluorosulfonate is added. After 5 minutes, a solution is otained and a temperature increase to 35° is observed. After stirring 2 hours at room temperature, the solution is evaporated to dryness, the residue is dissolved in water and the solution is extracted with ethyl acetate. The aqueous layer is made basic with sodium bicarbonate and extracted with ethyl acetate. This extract is then dried and evaporated to dryness to yield an oil that crystallizes when triturated in ether. Filtration affords 13.64 g. (88%) of D,L-N-formyl-α-methyl-3-(methylthiocarboximidato)tyrosine methyl ester, m.p. 140°-143° (dec.).

C. D,L-3-(Imidazol-2-yl)-α-Methyltyrosine Dihydrochloride

D,L-N-Formyl-α-methyl-3-(methylthiocarboximidato)-tyrosine methyl ester (8 g.; 25.8 mmoles), amino acetaldehyde diethyl acetal (3.4 g.; 25.6 mmoles), and oxalic acid (2.32 g.; 25.8 mmoles) in 200 ml. methanol is refluxed for 2 hours. The resulting mixture is evaporated to dryness, water (200 ml) is added to dissolve the residue and the solution is extracted with ethyl acetate. The aqueous layer is basified with solid sodium bicarbonate and washed with 100 ml of ether, 20 ml of ethyl acetate and evaporated to dryness. The residue from the aqueous solution is stirred vigorously with 200 ml of chloroform, which, after separation and drying is evaporated to dryness to yield 10 g. of an oil.

The oil (8.4 g) is dissolved in 100 ml concentrated hydrochloric acid, and the mixture refluxed for one hour. Evaporation to dryness yields D,L-3-(imidazol-2-yl)-α-methyltyrosine dihydrochloride, m.p. 160°-175° (dec.) (4.7 g.; 70%).

EXAMPLE 62

D,L-2-Methyl-3-(2-Methanesulfonylamidobenzimidazol-5-yl) Alanine Dihydrochloride Hemihydrate D,L-N-Formyl-3,4-diamino-α-methylphenylalanine methyl ester (4.0 g.; 16 mm) (prepared as in Step C of Example 26) and methyl N-methanesulfonylimino dithio carbonate (2.4 g.; 19.6 mmoles) in 20 ml. dimethyl formamide is heated overnight in an oil bath at 150°. The solvent is evaporated to a thick oil from which 2.37 g. (42%) D,L-N-formyl-2-methyl-3-(2-methanesulfonylamidobenzimidazol-5-yl)alanine methyl ester is isolated as a solid, m.p. 220°-225° (dec.) on trituration with 10 ml. ethanol. This ester (1 g.; 2.82 mmoles) is refluxed in 20 ml. concentrated hydrochlorice acid for 75 minutes. It is then cooled and evaporated under vacuum. The residue is redissolved again in water and taken back to dryness. This operation is repeated once more with water and then twice with ethanol to yield D,L-2-methyl-3-(3-methanesulfonylamidobenzimidazol-5-yl)alanine dihydrochloride hemihydrate (680 mg.;

EXAMPLE 63

D,L-2-Methyl-3-(2-amino-4-pyridyl)alaninedihydrochloride

A. 7-Bromomethyl tetrazolo[1,5-a]pyridine

7-Methyl tetrazolo [1,5-a]pyridine [Boyer, et al., J. Am. Chem. Soc., 82, 2218 (1960](23 g, 173 mmole), N-bromosuccinimide (30.6 g, 173 mmole) and benzoyl peroxide (100 mg) in 1.5 liters of benzene is refluxed overnight. More N-bromosuccinimide (15.3 g, 86.5 mole) is added and the reflux is maintained for several hours. The mixture is cooled and washed with 100 ml 20% sodium hydroxide and then with water. It is dried over calcium chloride, evaporated to dryness to yield 36.4 g of a mixture of 7-bromomethyltetrazolo [1,5-a]pyridine (63%) 7-dibromomethyltetrazolo [1,5-a]pyridine (24%) and 7-methyltetrazolo [1,5-a]pyridine (13%). Two triturations of this mixture with 500 ml of ether-hexane 1:1 (v/v) affords 25 g of a mixture consisting of 82% monobromo derivative, 13% dibromo derivative and 5% of starting material. This mixture is used for the next step.

B.
D,L-N-Formyl-2-methyl-3-(tetrazolo[1,5-a]pyrid-7-yl) alanine methyl ester Freshly prepared sodium methoxide (6 g, 113 mmole) is disolved in 100 ml dimethyl formamide and then cooled with an ice-bath to an internal temperature of 0°-5°. To this solution is added methyl 2-isocyanopropionate (12.8 g, 113 mmole). This solution is then added slowly to a solution of 7-bromomethyltetrazolo [1,5-a]pyridine (25 g of mixture; 94 mmole) in 40 ml of dimethyl formamide and maintaining the internal temperature around 5°. After the addition the mixture is allowed to warm up to room temperature. It is then poured into 1.5 liters of water and then extracted five times with 600 ml ethyl acetate. The ethyl acetate layers are combined, washed several times with water and dried over sodium sulfate. The dried solution is treated with charcoal and the volume is reduced to 1.5 liters. This solution is then treated with 1.5 ml concentrated hydrochloric acid at room temperature for 75 minutes. Water is added and decanted; the organic layer is washed with 5% sodium bicarbonate, with water and then dried over calcium chloride. The solution is evaporated to dryness and trituration with ether leaves 8.45 g (34%) of D,L-N-formyl-2-methyl-3-(tetrazolo[1,5-a]pyrid-7-yl) alanine methyl ester, m.p. 80°-85°.

C. D,L-2-Methyl-3-(2-amino-4-pyridyl)alanine dihydrochloride

D,L-N-Formyl-2-methyl-3-(tetrazolo[1,5-a]pyrid-7-yl)alanine methyl ester (4 g, 15.2 mmole) dissolved in 60 ml hydrochloric acid is heated on a steam bath until all starting material has disappeared as seen by TLC. Stannous chloride dihydrate (10.25 g, 45.6 mmole) is added in portions. The first additions give strong gas evolution. The mixture is then heated on steam bath for 105 minutes, after which is is evaporated to dryness. The residue is dissolved in 120 ml of water and hydrogen sulfide is bubbled through the solution. The precipitate filtered and the filtrate is treated with hydrogen sulfide again. The solid is filtered again and the filtrate is evaporated to dryness. The residue is triturated with 50 ml acetonitrile and filtration yields 2.66 g (66%) of D,L-2-methyl-3-(2-amino-4-pyridyl)alanine dihydrochloride, m.p. 258°-260°.

EXAMPLE 64

D,L-2-Methyl-3-(tetrazolo[1,5-a]pyrid-7-yl)alanine hydrochloride

D,L-N-Formyl-2-methyl-3-(tetrazolo[1,5-a]pyrid-7-yl)alanine methyl ester (4.0 g, 15.2 mmole), prepared as in part B of Example 63, is refluxed in 50 ml concentrated hydrochloric acid for 5 hours. On cooling, some solid impurities are filtered and discarded. The filtrate is taken down to dryness, redissolved in 200 ml water and left in the refrigerator for 18 hours. The solid is removed by filtration, the filtrate is treated with activated charcoal and then evaporated to dryness. The residue is triturated with 50 ml hot isopropanol and filtered to yield 2.37 g (60%) of D,L-2-methyl-3-(tetrazolo[1,5-]pyrid-7-yl)alanine hydrochloride, m.p. 240°-245°.

EXAMPLE 65

D,L-3-cyano-α-methylphenylalanine methyl ester hydrochloride

A solution of 56 g (0.245 mole) of methyl D,L-3-(3-cyanophenyl)-2-isocyano-2-methyl propionate (prepared as in part A of Example 2) in 500 ml of ethyl acetate is cooled in an ice bath. To the cooled and stirred solution is added 23 ml of concentrated hydrochloric acid, the ice bath is removed and the mixture stirred at 25° for 2 hours. The solution is washed with 3 × 200 ml of water and the aqueous extract is made basic with solid sodium carbonate. Extraction of the basic solution with 2 × 100 ml of ether, drying of the etheral extract and passage of gaseous hydrogen chloride into the dried ether solution gives a precipitate which is filtered and dried to yield 4.27 g (6.9%) of D,-3-cyano-α-methylphenylalanine methyl ester hydrochloride, m.p. 160°-165°.

EXAMPLE 66

D,L-α-Methyl-3-(4-trifluoromethylthiazol-2-yl)tyrosine hydrochloride

A. D,L-3-(4,5-Dihydro-4-hydroxy-4-trifluoromethyl-thiazol-2-yl)-N-formyl-α-methyltyrosine methyl ester A mixture of 3.5 g (18 mm) of 3-bromo-1,1,1-trifluoropropanone, 150 ml of acetonitrile and 5 g (17 mm) of D,L-N-formyl-α-methyl-3-thiocarbamoyltyrosine methyl ester, described in part A of Example 61, is magnetically stirred at reflux for 30 minutes. The solution is evaporated to dryness and the gummy residue triturated with ethyl acetate. The product is filtered and washed with a small volume of diethyl ether to yield 7.5 g of crude (97%) D,L-3-(4,5-dihydro-4-hydroxy-4-trifluoromethylthiazol-2-yl)-N-formyl-α-methyltyrosine methyl ester which is of sufficient quality for the next step.

B. D,L-α-Methyl-3-(4-trifluoromethylthiazol-2-yl)tyrosine hydrochloride

A mixture of 100 ml of concentrated HCl and 7.5 g (18 mm) of D,L-3-(4,5-dihydro-4-hydroxy-4-trifluoromethyl-thiazol-2-yl)-N-formyl-α-methyltyrosine methyl ester is refluxed for one hour. After cooling, the crystals are filtered and washed with diethyl ether. The solid is dried at 50° under vacuum for 3 hours to yield 3.4 g (50%) of D,L-α-methyl-3-(4-trifluoromethyl-thiazol-2-yl)tyrosine hydrochloride, m.p. 285° (dec.)

EXAMPLE 67

| PREPARATION OF CAPSULE FORMULATION | |
| --- | --- |
| Ingredient | Milligrams per Capsule |
| α-Methyl-3-(4-trifluoromethyl-thiazol-2-yl)phenylalanine | 40 |
| Starch | 440 |
| Magnesium stearate | 5 |

The active ingredient, starch and magnesium stearate are blended together. The mixture is used to fill hard shell capsules of a suitable size at a fill weight of 485 milligrams per capsule.

| PREPARATION OF TABLET FORMULATION | |
| --- | --- |
| Ingredient | Milligrams per Tablet |
| 4-(Imidazol-2-yl)-α-methyl-phenylalanine | 25 |
| Lactose | 200 |
| Corn starch (for mix) | 50 |
| Corn starch (for paste) | 50 |
| Magnesium stearate | 6 |

The active ingredient, lactose and corn starch (for mix), are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 25 milligrams of active ingredient.

EXAMPLE 69

| PREPARATION OF ORAL SYRUP FORMULATION | |
| --- | --- |
| Ingredient | Amount |
| α-Methyl-4-(pyrrol-1-yl)phenylalanine | 50 mg. |
| Sorbitol solution (70% N.F.) | 40 ml. |
| Sodium benzoate | 150 mg. |
| Saccharin | 50 mg. |
| Red Dye (F.D & C. No. 40) | 10 mg. |
| Cherry flavor | 50 mg. |
| Distilled water qs to | 100 ml. |

The sorbitol solution is added to 40 milliliters of distilled water and the active ingredient is suspended therein. The saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:

1. A compound of the formula:

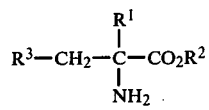

wherein $R^1$ and $R^2$ are hydrogen or lower alkyl and $R^3$ is 1-H-2-oxindol-5-yl.

2. A compound of claim 1 wherein $R^1$ is methyl and $R^2$ is hydrogen.

3. A composition for treating hypertension comprising a therapeutically effective amount of a compound of claim 1 in combination with a pharmaceutically acceptable carrier.

4. A method of treating hypertension in a patient in need of said treatment which comprises administering thereto a blood pressure reducing amount of a compound of claim 1.

5. A method of treating hypertension in a patient in need of said treatment which comprises administering thereto a blood pressure reducing amount of the compound of claim 2.

* * * * *